US011064956B2

(12) United States Patent
Defreitas et al.

(10) Patent No.: US 11,064,956 B2
(45) Date of Patent: Jul. 20, 2021

(54) BREAST COMPRESSION PADDLE HAVING AN INFLATABLE JACKET

(71) Applicant: HOLOGIC, INC., Marlborough, MA (US)

(72) Inventors: Kenneth F. Defreitas, Marlborough, MA (US); Timothy R. Stango, Marlborough, MA (US)

(73) Assignee: HOLOGIC, INC., Marlborough, MA (US)

( * ) Notice: Subject to any disclaimer, the term of this patent is extended or adjusted under 35 U.S.C. 154(b) by 0 days.

(21) Appl. No.: 16/638,181

(22) PCT Filed: Aug. 10, 2018

(86) PCT No.: PCT/US2018/046304
§ 371 (c)(1),
(2) Date: Feb. 11, 2020

(87) PCT Pub. No.: WO2019/033022
PCT Pub. Date: Feb. 14, 2019

(65) Prior Publication Data
US 2020/0359974 A1 Nov. 19, 2020

Related U.S. Application Data

(60) Provisional application No. 62/544,374, filed on Aug. 11, 2017.

(51) Int. Cl.
*A61B 6/04* (2006.01)
*A61B 6/00* (2006.01)
*A61B 6/02* (2006.01)

(52) U.S. Cl.
CPC ............ *A61B 6/0414* (2013.01); *A61B 6/025* (2013.01); *A61B 6/502* (2013.01)

(58) Field of Classification Search
CPC ....... A61B 6/0414; A61B 6/025; A61B 6/502; A61B 6/0485
See application file for complete search history.

(56) References Cited

U.S. PATENT DOCUMENTS 3,971,950 A 7/1976 Evans et al.
4,496,557 A 1/1985 Malen
(Continued)

FOREIGN PATENT DOCUMENTS

CN 105286904 2/2016
EP 955886 11/1999
(Continued)

OTHER PUBLICATIONS

PCT International Preliminary Report on Patentability in International Application PCT/US2017/053311, dated May 14, 2019, 13 pgs.
(Continued)

*Primary Examiner* — Courtney D Thomas

(57) ABSTRACT

A breast compression paddle for use in an imaging system includes a compression surface and a jacket. The jacket includes at least one inflatable chamber disposed adjacent to the compression surface and a sheet covering at least a portion of the compression surface. The at least one inflatable chamber is configured to selectively inflate and induce the sheet to slide along the compression surface.

20 Claims, 18 Drawing Sheets

(56) References Cited

U.S. PATENT DOCUMENTS

| | | |
|---|---|---|
| 4,943,986 A | 7/1990 | Barbarisi |
| 5,051,904 A | 9/1991 | Griffith |
| 5,359,637 A | 10/1994 | Webber |
| 5,506,877 A | 4/1996 | Niklason |
| 5,553,111 A | 9/1996 | Moore et al. |
| D376,012 S | 11/1996 | Hixson, Sr. |
| 5,706,327 A | 1/1998 | Adamkowski |
| 6,289,235 B1 | 9/2001 | Webber |
| 6,647,092 B2 | 11/2003 | Eberhard |
| 7,123,684 B2 | 10/2006 | Jing et al. |
| 7,245,694 B2 | 7/2007 | Jing et al. |
| 7,430,272 B2 | 9/2008 | Jing et al. |
| 7,583,786 B2 | 9/2009 | Jing et al. |
| 7,831,296 B2 | 11/2010 | Defreitas |
| 7,869,563 B2 | 1/2011 | Defreitas et al. |
| 8,175,219 B2 | 5/2012 | DeFreitas et al. |
| 8,787,522 B2 | 7/2014 | Smith et al. |
| 9,050,009 B2 | 6/2015 | Den Heeten |
| 9,226,718 B1 | 1/2016 | Baxley |
| 9,332,947 B2 | 5/2016 | DeFreitas et al. |
| 9,498,180 B2 | 11/2016 | Ren et al. |
| 9,743,997 B2 | 8/2017 | Grimbergen |
| 9,782,135 B2 | 10/2017 | Stango et al. |
| 9,826,950 B2 | 11/2017 | Den Heeten |
| 10,603,002 B2 | 3/2020 | Stango |
| 2001/0038861 A1 | 11/2001 | Hsu |
| 2002/0061090 A1 | 5/2002 | Lindstrom |
| 2004/0066882 A1 | 4/2004 | Eberhard |
| 2004/0066884 A1 | 4/2004 | Claus |
| 2004/0066904 A1 | 4/2004 | Eberhard |
| 2004/0218727 A1 | 11/2004 | Shoenfeld |
| 2005/0008117 A1 | 1/2005 | Livingston |
| 2005/0063509 A1 | 3/2005 | DeFreitas et al. |
| 2005/0113681 A1 | 5/2005 | DeFreitas et al. |
| 2005/0113683 A1 | 5/2005 | Lokhandwalla et al. |
| 2007/0223652 A1 | 9/2007 | Galkin |
| 2007/0242794 A1 | 10/2007 | Stanton |
| 2007/0280412 A1 | 12/2007 | Defreitas et al. |
| 2008/0080668 A1 | 4/2008 | Kashiwagi |
| 2009/0262887 A1 | 10/2009 | Iordache et al. |
| 2009/0268865 A1 | 10/2009 | Ren |
| 2010/0046698 A1 | 2/2010 | Lebovic et al. |
| 2011/0257919 A1 | 10/2011 | Reiner |
| 2012/0277625 A1 | 11/2012 | Nakayama |
| 2013/0272493 A1 | 10/2013 | Otokuni |
| 2014/0296701 A1 | 10/2014 | Hancu et al. |
| 2014/0328458 A1 | 11/2014 | Erhard et al. |
| 2015/0272682 A1* | 10/2015 | Sheng ............... A61B 90/14 128/845 |
| 2015/0282770 A1 | 10/2015 | Klanian et al. |
| 2016/0081633 A1 | 3/2016 | Stango et al. |
| 2016/0242707 A1* | 8/2016 | DeFreitas ............. A61B 6/025 |
| 2017/0340303 A1 | 11/2017 | Stango |
| 2018/0165840 A1 | 6/2018 | Bernard |
| 2020/0069274 A1 | 3/2020 | Stango |
| 2020/0178926 A1 | 6/2020 | Kshirsagar |
| 2020/0196971 A1 | 6/2020 | Laviola |
| 2020/0359975 A1 | 11/2020 | Banks |

FOREIGN PATENT DOCUMENTS

| | | |
|---|---|---|
| EP | 2341832 A1 | 7/2011 |
| EP | 2943125 A1 | 11/2015 |
| JP | S53-103672 | 8/1978 |
| JP | H03-86154 | 4/1991 |
| JP | 2011-072667 | 4/2011 |
| JP | 2011-250842 | 12/2011 |
| JP | 2015-027382 A | 2/2015 |
| KR | 10-2011-0089446 | 8/2011 |
| KR | 10-2014-0058066 | 5/2014 |
| NL | 2020910 B1 | 11/2019 |
| WO | 2010/028208 | 3/2010 |
| WO | 2010/102087 | 9/2010 |
| WO | 2011/058730 | 5/2011 |
| WO | 2014/074602 A1 | 5/2014 |
| WO | 2014/176445 | 10/2014 |
| WO | 2015/054518 | 4/2015 |
| WO | 2016/073445 A1 | 5/2016 |
| WO | 2018/067005 | 4/2018 |
| WO | 2018/089118 | 5/2018 |
| WO | 2018/170265 | 9/2018 |
| WO | 2019/004821 | 1/2019 |
| WO | 2019/088826 | 5/2019 |

OTHER PUBLICATIONS

PCT International Preliminary Report on Patentability in International Application PCT/US2018/046304, dated Feb. 11, 2020, 13 pgs.

PCT International Preliminary Report on Patentability in International Application PCT/US2018/046312, dated Feb. 11, 2020, 11 pgs.

Digital Clinical Reports, Tomosynthesis (GE Brochure 98/5493, Nov. 1998), 8 pgs.

European Extended Search Report in Application 15857678.5, dated Jun. 26, 2018, 8 pages.

Grant, D.G., "Tomosynthesis: a three-dimensional imaging technique", IEEE Trans. Biomed. Engineering, vol. BME-19, #1, (Jan. 1972), pp. 20-28.

PCT International Preliminary Report on Patentability in International Application PCT/US2015/058782, dated May 18, 2017, 10 pgs.

PCT International Search Report and Written Opinion of the International Searching Authority for corresponding International Patent Application No. PCT/US2015/058782 dated Feb. 17, 2016, 14 pgs.

PCT International Search Report and Written Opinion of the International Searching Authority for International Patent Application No. PCT/US2017/053311 dated Mar. 6, 2018, 21 pages.

PCT International Search Report and Written Opinion of the International Searching Authority for International Patent Application No. PCT/US2018/046312 dated Dec. 11, 2018, 14 pages.

U.S. Appl. No. 60/628,516 entitled "Matching geometry generation and display of mammograms and tomosynthesis images", filed Nov. 15, 2004, 20 pgs.

International Search Report and Written Opinion of the International Searching Authority for International Patent Application No. PCT/US2018/046304 dated Dec. 11, 2018, 18 pages.

PCT International Preliminary Report on Patentability in International Application PCT/IB2018/056208, dated Feb. 27, 2020, 10 pages.

PCT International Search Report and Written Opinion in International Application PCT/IB2018/056208, dated Nov. 13, 2018, 12 pages.

European Extended Search Report in Application 188437883, dated Mar. 29, 2021, 16 pages.

European Communication and Search Report in Application 18847121.3, dated Apr. 8, 2021, 5 pages.

\* cited by examiner

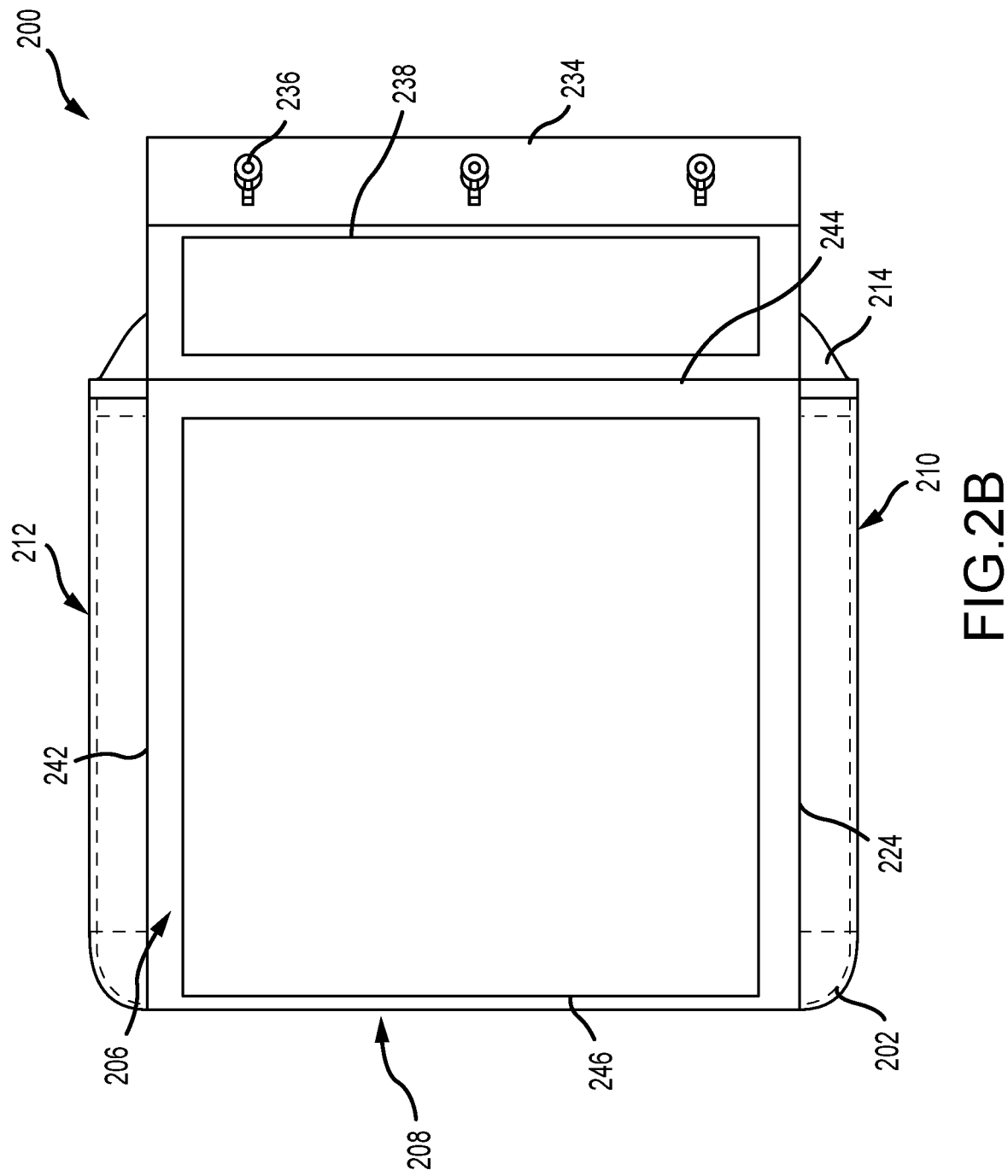

BREAST COMPRESSION PADDLE HAVING AN INFLATABLE JACKET

CROSS-REFERENCE TO RELATED APPLICATIONS

This application is a National Stage Application of PCT/US2018/046304, filed Aug. 10, 2018, which claims priority to and the benefit of U.S. Provisional Patent Application No. 62/544,374, filed on Aug. 11, 2017, the disclosure of which are hereby incorporated by reference in their entireties. To the extent appropriate, a claim of priority is made to each of the above disclosed applications.

BACKGROUND

Compression during mammography and tomosynthesis imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the image plane over the entire breast image; (3) immobilizes the breast during the x-ray exposure and thereby reduces image blurring; and (4) brings breast tissues out from the chest wall into the imaging exposure field and thus allows for more tissue imaging. As the breast is being compressed, typically a technologist manipulates the breast to position it appropriately and counter the tendency that compression has of pushing breast tissue toward the chest wall and out of the image field.

Standard compression methods for mammography and tomosynthesis use a movable, rigid, radiolucent compression paddle. The breast is placed on a breast support platform that typically is flat, and the paddle then compresses the breast, usually while a technologist or other health professional is holding the breast in place. The technologist may also manipulate the breast to ensure proper tissue coverage in the image receptor's field of view.

One known challenge in mammography and breast tomosynthesis is the discomfort the patient may feel when the breast is compressed, which must be done with sufficient force to immobilize the breast and spread out the breast tissues for x-ray imaging. Another known challenge is to ensure that the imaged field includes the desired amount of breast tissue.

SUMMARY

In one aspect, the technology relates to a breast compression paddle for use in an imaging system, the breast compression paddle including: a compression surface; and a jacket including at least one inflatable chamber disposed adjacent to the compression surface and a sheet covering at least a portion of the compression surface, wherein the at least one inflatable chamber is configured to selectively inflate and induce the sheet to slide along the compression surface.

In an example, the sheet includes at least one cushioning chamber covering at least a portion of the compression surface. In another example, the at least one cushioning chamber is configured to selectively inflate. In yet another example, the at least one cushioning chamber is configured to inflate to a pressure that is lower than a pressure of the at least one inflatable chamber. In still another example, the inflation pressure of the at least one inflatable chamber and the inflation pressure of the at least one cushioning chamber are independently controlled. In an example, the at least one cushioning chamber includes a plurality of chambers.

In another example, the breast compression paddle further includes a bracket or integral feature having a recess defined adjacent to the compression surface, wherein the at least one inflatable chamber is disposed proximate the bracket or integral feature and is configured to selectively inflate at least partially into the recess. In yet another example, the sheet is configured to slide along the compression surface substantially simultaneously with the at least one inflatable chamber selectively inflating. In still another example, the breast compression paddle further includes a top surface opposite the compression surface, wherein the jacket substantially surrounds the top surface and the compression surface. In an example, the breast compression paddle further includes a bracket or integral feature, and wherein the jacket further includes a first edge coupled to the bracket or integral feature adjacent the top surface.

In another aspect, the technology relates to an imaging system including: an imaging source; an imaging receptor defining an imaging area; and a breast compression unit including: a breast compression paddle having a first compression surface; a platform having a second compression surface, wherein the breast compression paddle is configured to move in relation to the platform to compress a patient's breast between the first compression surface and the second compression surface; and a paddle jacket disposed on the breast compression paddle such that the first compression surface is at least partially covered, the paddle jacket including at least one inflatable chamber and a sheet, wherein the at least one inflatable chamber is configured to selectively inflate and induce the sheet to slide along the first compression surface.

In an example, the imaging system further includes a platform jacket disposed on the platform such that the second compression surface is at least partially covered, the platform jacket including at least one inflatable chamber and a sheet, wherein the at least one inflatable chamber is configured to selectively inflate and induce the sheet to slide along the second compression surface. In another example, the paddle jacket is independently inflatable from the platform jacket. In yet another example, the imaging system further includes a fluid source configured to deliver a flow of fluid to the paddle jacket for the selective inflation of the at least one inflatable chamber. In still another example, the paddle jacket is removably disposed on the breast compression paddle. In an example, the breast compression paddle is removable from the breast compression unit.

In another aspect, the technology relates to a method of compressing a breast in an imaging system including a jacket having at least one inflatable chamber and a sheet, the method including: compressing a breast between a compression paddle and a platform; selectively inflating the at least one inflatable chamber of the jacket disposed on the breast compression paddle such that the sheet slides along a compression surface and pulls at least some breast tissue away from a patient's chest wall and into an imaging area.

In an example, the sheet includes at least one cushioning chamber disposed below the compression surface, and the method further includes after the breast is compressed between the compression paddle and the platform selectively inflating the at least one cushioning chamber. In another example, the at least one inflatable chamber is selectively inflated to a different pressure than a pressure of the at least one cushioning chamber. In yet another example, the method further includes removably attaching the jacket on the breast compression paddle; and coupling in fluid communication the jacket to a fluid source.

In another aspect, the technology relates to a breast compression unit for an x-ray imaging system, the breast compression unit including: a support platform including a compression surface; a compression paddle movably disposed relative to the support arm such that a patient breast can be compressed between the compression paddle and the compression surface, wherein the compression paddle is angled relative to the compression surface; and a jacket including at least one inflation chamber coupled to the compression paddle, wherein the at least one inflation chamber includes an edge section disposed proximate a front surface of the compression paddle, and wherein when the at least one inflation chamber is inflated a slope of the edge section is substantially parallel to the compression surface.

In an example, the compression paddle has a bottom surface adjacent to the at least one inflation chamber, and wherein the bottom surface is substantially planar. In another example, the compression paddle has a bottom surface adjacent to the at least one inflation chamber, and wherein the bottom surface is substantially curved.

In another aspect, the technology relates to a breast compression unit for an x-ray imaging system, the breast compression unit including: a support platform including a compression surface; and a compression paddle movably coupled to the support arm, wherein the compression paddle is moveable along a first axis substantially orthogonal to the compression surface and along a second axis substantially parallel to the compression surface.

In an example, a first drive system is coupled to the compression paddle and configured to move the compression paddle along the first axis, and a second drive system is coupled to the compression paddle and configured to move the compression paddle along the second axis. In another example, the movement of the compression paddle along the first axis occurs substantially simultaneously with movement along the second axis. In yet another example, the movement of the compression paddle along the first axis is discrete from movement along the second axis.

In another aspect, the technology relates to a breast support platform for an x-ray imaging system, the breast support platform including: a compression surface; a front surface disposed at an angle to the compression surface and configured to contact a chest wall of a patient during a compression of a breast against the compression surface; and an inflatable membrane disposed at the front surface and configured to receive a fluid and expand at least partially away from the front surface so as to form a cushioned element on the breast support platform.

In an example, the inflatable member is disposed at least partially within a recess defined by the front surface and is covered by a flexible cover. In another example, a flexible cover includes the inflatable membrane, and wherein the flexible cover is removably coupled to the front surface.

In another aspect, the technology relates to a compression element for an x-ray imaging system, the compression element including: a structural support; and an inflatable bladder coupled to the structural support, wherein the inflatable bladder forms both a front wall and a compression surface of the compression element, and wherein the inflatable bladder is configured to receive a flow of fluid and selectively release the fluid upon compression of a patient breast.

In an example, a bleed valve is coupled to the inflatable bladder and is configured to selectively release the fluid upon compression of the patient breast. In another example, the compression element further includes a reservoir coupled in flow communication with the inflatable bladder, and wherein the fluid released from the inflatable bladder is channeled to the reservoir. In yet another example, the inflatable bladder includes one or more support tubes configured to at least partially define a shape of the front wall. In still another example, the structural support includes two or more arms.

In another aspect, the technology relates to a method of compressing a breast for an imaging procedure on an x-ray imaging system, the method including: moving a compression element towards a support platform, wherein the compression element includes a structural support and an inflatable bladder filled with a fluid; contacting the breast with the compression element such that a compressive load is applied to the breast, and the breast compresses between the compression element and the support platform; and upon reaching a predetermined compressive force on the breast, selectively releasing at least a portion of the fluid from the inflatable bladder such that any further applied compressive load does not increase the compressive force on the breast.

In an example, the method further includes attaching the inflatable bladder to the structural support. In another example, attaching the inflatable bladder includes tensioning the inflatable bladder between a pair of arms. In yet another example, electively releasing fluid from the inflatable bladder includes bleeding air to the atmosphere. In still another example, prior to moving the compression element, the method further includes inflating the inflatable bladder with the fluid.

BRIEF DESCRIPTION OF THE DRAWINGS

FIG. 2B is a bottom view of the breast compression system of FIG. 2A.

DETAILED DESCRIPTION

Figure 1A:
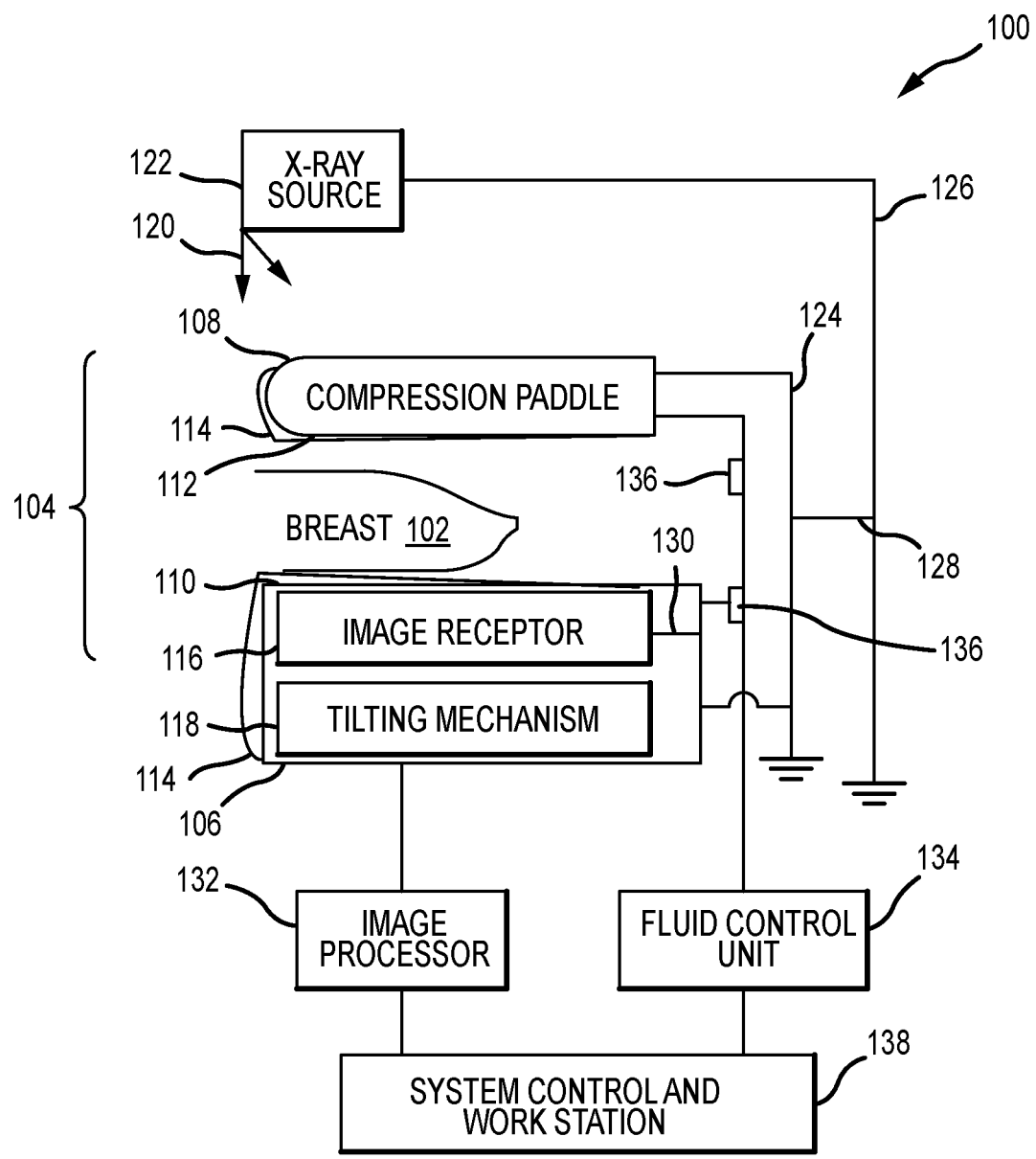
FIG. 1A is a schematic view of an exemplary imaging system.

The present technology relates to a breast compression system having a breast compression paddle or compression support surface, an inflatable jacket, inflation control, and/or other components as described below for use in a breast imaging system. During imaging of a breast, it is often desirable to immobilize the breast through compression. For instance, by compressing the breast, the breast can be made thinner, thus requiring a lower dose of radiation. Further, by immobilizing the breast, image blurring from movement of the breast during imaging is reduced. Other benefits may also be realized by compressing the breast. The paddle commonly used to compress the breast, however, may cause distortions in the imaging process. For instance, during compression, the breast tissue may become rolled or folded, or may be pushed into the chest wall, thereby changing the profile of the compressed breast.

The paddle may also cause discomfort to the patient whose breast is being compressed. One reason for discomfort that the patient may feel is that the compression force is non-uniformly distributed throughout the breast. It is often concentrated at the thickest portion of the breast, usually near the chest wall, at or near the lower front edge of the compression paddle and the upper front corner of the breast platform. The anterior portion of the breast, such as near the nipple, may receive less compressive force, or no compressive force. The paddle may not even contact this portion of the breast. Other reasons for discomfort may be over-compression of the breast by the paddle. (The terms front, lower, and upper pertain to using a craniocaudal (CC) imaging orientation, with the patient facing the front of the imaging system, although it should be understood that other imaging orientations, including mediolateral oblique (MLO), are used with the same equipment.)

To improve these issues relating to the compression systems, the compression systems described herein include an inflatable jacket that is positioned over a compression surface and is configured to receive a flow of fluid so as to selectively inflate or deflate. During breast compression, the jacket is selectively inflated so as to pull breast tissue away from the chest wall and into the imaging area. Additionally, the jacket reduces rolling and folding of the breast tissue so as to maintain a more desirable breast profile. In one example, the breast compression occurs substantially simultaneously with the inflation of the jacket. The inflatable jacket provides more comfort to the patient during breast compression because the pulling sensation is reduced while increasing the volume of breast tissue within the imaging area. After breast compression, the jacket may further be selectively inflated so as to reduce breast tissue wrinkling and provide further comfort to the patient while the breast is imaged.

Additionally, the technologies described herein provide compression systems that reduce breast tissue being pushed into the chest wall so that as much breast tissue as possible is pulled into the imaging area. This can be enabled by angling the compression paddle that the inflatable jacket is coupled to. Additionally or alternatively, fluid flow may be directed to an inflatable membrane that is positioned on a front wall of the support platform so that a cushioned support may be provided to the patient. This increases overall patient comfort during imaging procedures. Moreover, an inflatable bladder on the compression paddle may be used to decrease over-compression of the patient's breast. For example, during the compression procedure, the bladder may be selectively inflated or deflated so that the compressive force induced on the breast is limited to a predetermined value. This also increases overall patient comfort during imaging procedures. Further technologies described herein include a mechanical system that pulls breast tissue away from the chest wall and into the imaging area without the need of a flow of fluid and an inflatable jacket.

Figure 1B:
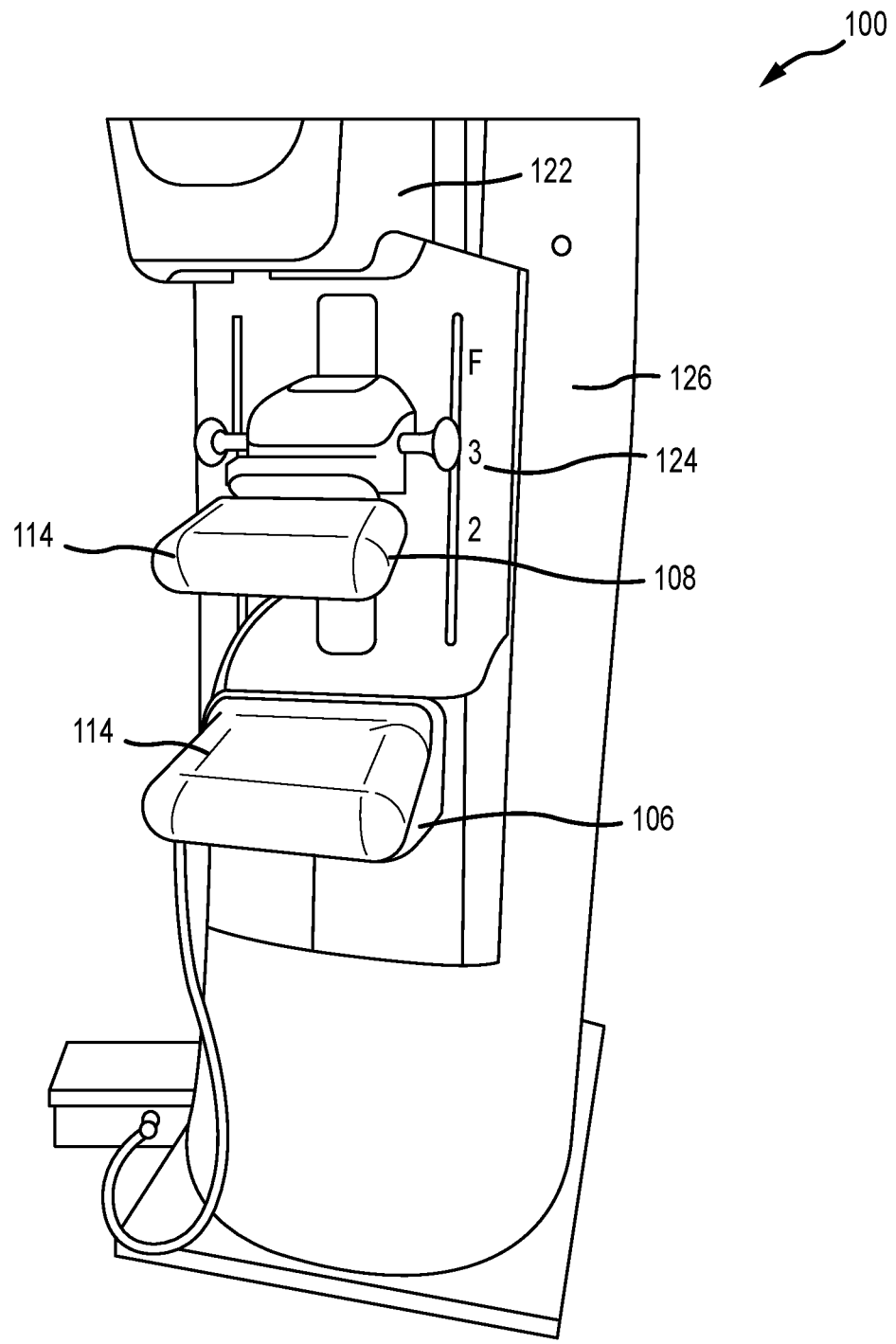
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, the imaging system 100 immobilizes a patient's breast 102 for x-ray imaging (either or both of mammography and tomosynthesis) via a breast compression immobilizer unit 104 that includes a static breast support platform 106 and a moveable compression paddle 108. The breast support platform 106 and the compression paddle 108 each have a compression surface 110 and 112, respectively, and at least one compression surface move towards the other, to compress and immobilize the breast 102. In the example, both the platform 106 and the paddle 108 include an inflatable jacket 114, which is described further below in reference to FIGS. 2A-2C. In other examples, only one of the platform 106 or the paddle 108 may include the inflatable jacket 114. When no inflatable jacket 114 is utilized, the compression surface 110, 112 is exposed so as to directly contact the breast 102. The platform 106 also houses an image receptor 116 and, optionally, a tilting mechanism 118. The immobilizer unit 104 is in a path of an imaging beam 120 emanating from x-ray source 122, such that the beam 120 impinges on the image receptor 116.

The immobilizer unit 104 is supported on a first support arm 124 and the x-ray source 122 is supported on a second support arm 126. For mammography, support arms 124 and 126 can rotate as a unit about an axis 128 between different imaging orientations such as CC and MLO, so that the system 100 can take a mammogram projection image at each orientation. In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The system 100 takes plural tomosynthesis projection images of the breast 102 at respective angles of the beam 120 relative to the breast 102.

Concurrently and optionally, the image receptor 116 may be tilted relative to the breast support platform 106 and coordinated with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging. An example of such a combo system is been offered by the assignee hereof under the trade name Selenia Dimensions.

When the system is operated, the image receptor 116 produces imaging information in response to illumination by the imaging beam 120, and supplies it to an image processor 132 for processing and generating breast x-ray images. A fluid control unit 134 connects with the compression paddle 108 and the platform 106 to selectively provide fluid air into the jackets 114 and increase breast tissue drawn into the imaging during breast compression and comfort of the patient, as described herein. The fluid control unit 134 can be powered by an operator, using a hand-pump or a foot pump and appropriate manual or foot-controlled valves, or alternatively, electric or fluid-powered pumps can be used, with appropriate valves and interfaces such as buttons or switches that the operator controls. In another example, the fluid control unit 134 is automatically controlled by one or more sensors, such as position sensors and pressure sensors, in or on the compression paddle 108, platform 106, inflatable jackets 114, and/or any other component and software that may enable the user to control the system. In an example, the fluid control unit 134 connects via a quick-release snap-on connection 136, or the like, to the inflatable jacket 144 so as to provide a flow of fluid thereto. A system control and work station unit 138 including software controls the operation of the system and interacts with the operator to receive commands and deliver information including processed-ray images. In some examples, the paddle jacket 114 is independently inflated from the platform jacket 114.

One challenge with the imaging system 100 is how to immobilize and compress the breast 102 for the desired or required imaging. A health professional, typically an x-ray technologist, generally adjusts the breast 102 within the immobilizer unit 104 while pulling tissue towards imaging area and moving the compression paddle 108 toward the breast support platform 106 to immobilize the breast 102 and keep it in place, with as much of the breast tissue as practicable being between the compression surfaces 110, 112. However, it may be desirable to further compress or otherwise act on the breast 102 so that breast tissue can be pulled away from the patient's chest wall and securely retained in the immobilizer unit 104 for imaging. Accordingly, and for increasing patient comfort and breast compression profile, the breast support platform 106 and the compression paddle 108 includes the inflatable jacket 114 that has at least one inflatable chamber to enable breast tissue to be pulled away from the chest wall during breast compression in order to obtain a desired breast compression profile and provide a greater amount of compression comfort to the patient. These breast compression systems are described in further detail below.

Figure 2A:
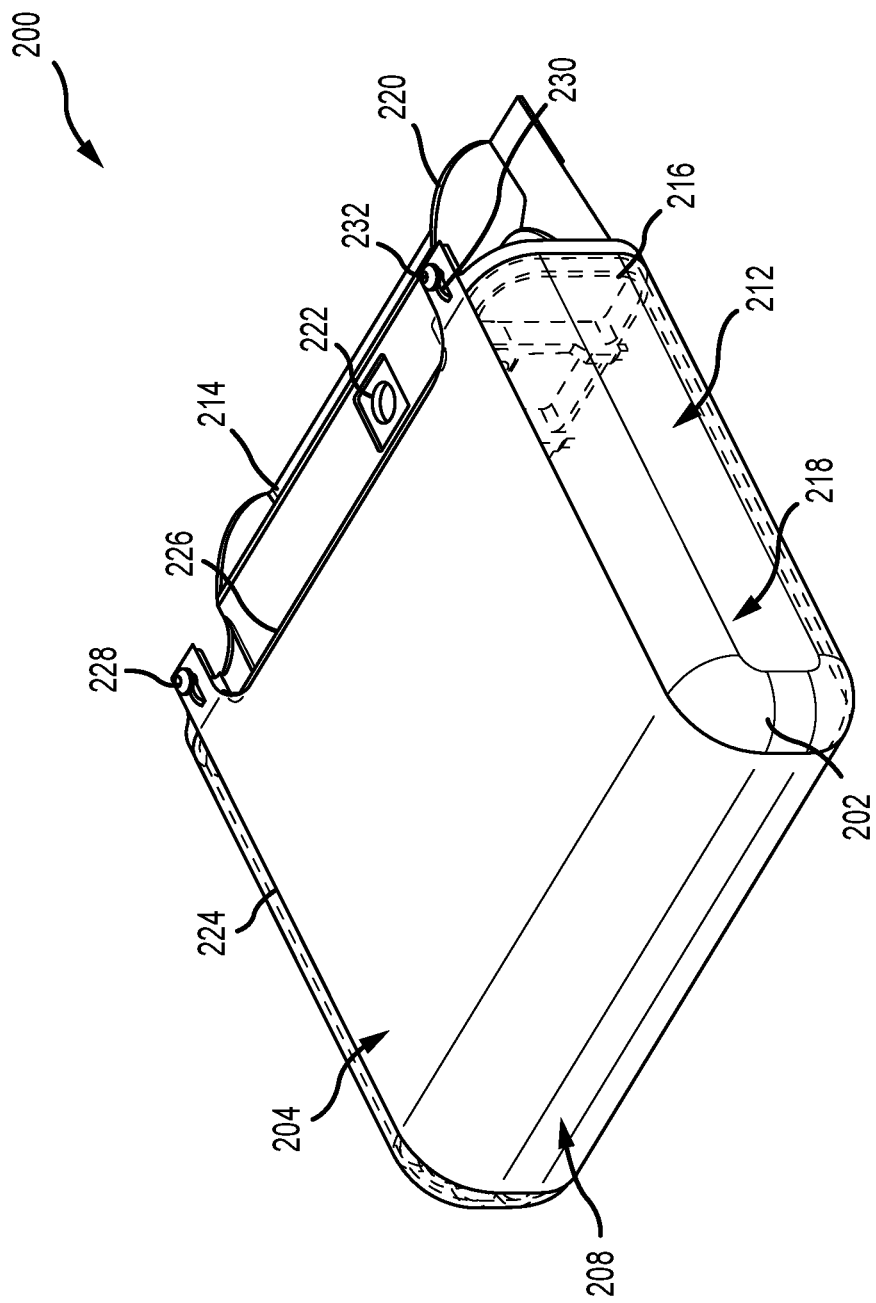
FIG. 2A is a top perspective view of an exemplary breast compression system.
Figure 2C:
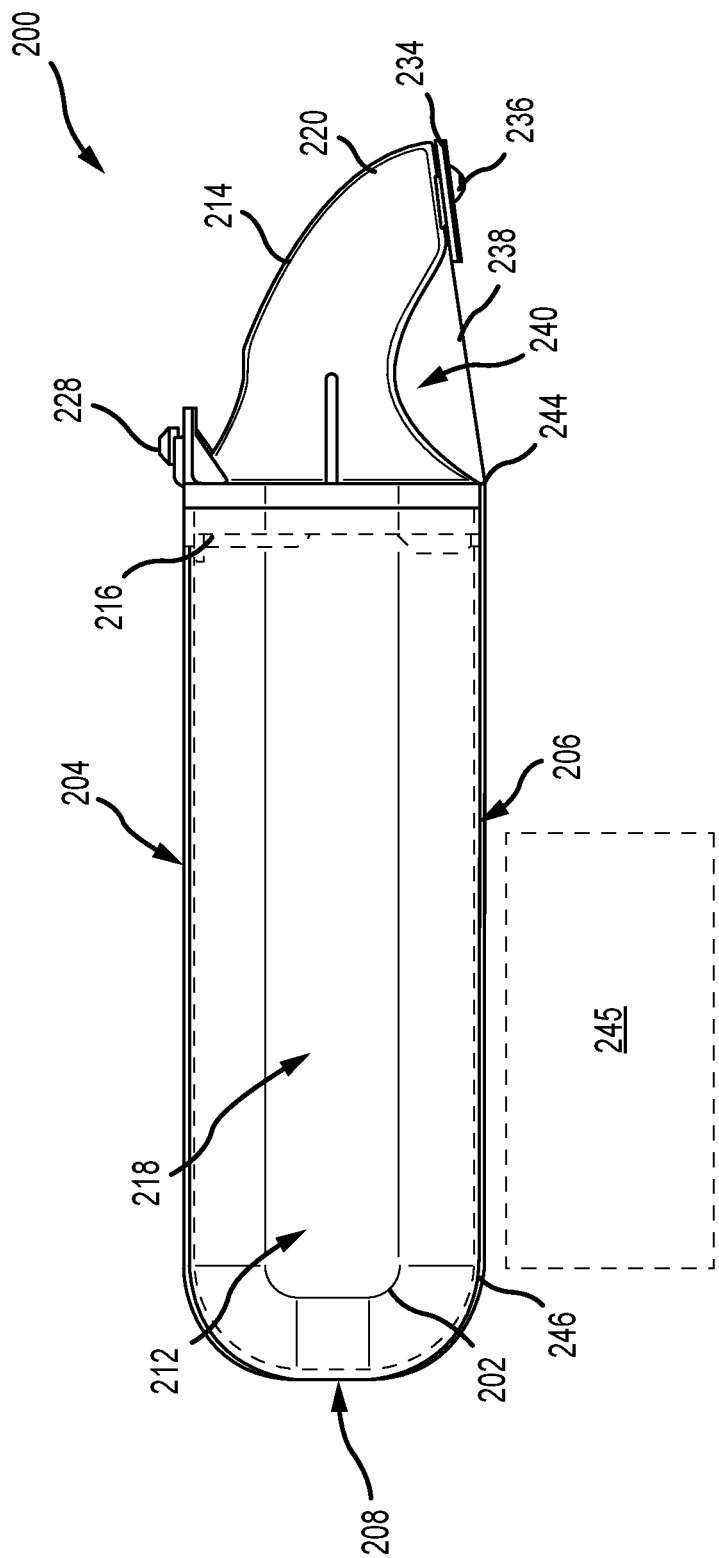
FIG. 2C is a side view of the breast compression system of FIG. 2A.

FIGS. 2A-2C illustrate an exemplary breast compression system 200. Referring concurrently to FIGS. 2A-2C, the breast compression system 200 may be utilized as a breast compression paddle or a breast support platform. The breast compression system 200 includes body 202 defined by a top surface 204 and an opposite bottom surface 206. In general, surfaces of the breast compression system 200 are described as depicted in the figures (e.g., "top," "bottom," etc.). These general terms are utilized for clarity and only to distinguish the various surfaces from each other. For instance, in FIGS. 2A-2C, the top surface 204 is a non-compression surface while the bottom surface 206 is a compression surface. The body 202 is also defined by a front surface 208, a left surface 210, and a right surface 212. In the example, the body 202 is hollow and may be manufactured from a material that is designed to cause minimal interference with the radiation beam passing through the breast compression system 200, such as a radiolucent material. For example, the body 202 may be made from a polycarbonate material, a carbon fiber material, or other similar materials. In alternative examples, the body 202 may be solid, or partially filled. Additionally, in alternative examples, the body 202 may have an open top surface 204, for example, as illustrated by the compression paddle 312 (shown in FIGS. 4A-4C).

In the example, the body 202 is coupled to a bracket 214 positioned opposite the front surface 208. The bracket 214 includes an end 216 that is received within an interior chamber 218 of the body 202, or that may be secured to an end thereof. An extension 220 extends from the end 216 and away from the body 202. The extension 220 is configured to be removably attached to a compression assembly of an imaging system. The bracket 214 may also include an inlet port 222 disposed on the top of the bracket 214 that is in fluidic communication with the interior chamber 218. Optionally, heated fluid, such as warm air or gas, may be injected into the interior chamber 218 via the inlet port 222 to warm the breast compression system 200 before and/or during contact with the breast. In alternative examples, the body 202 may be integral with the bracket 214 so that the breast compression system 200 has a first portion (e.g., the bottom surface 206) that forms a breast compression surface and an integral opposite second portion that enables the system 200 to be removably attached to the compression assembly, for example, as illustrated by the compression paddle 312 (shown in FIGS. 4A-4C).

The breast compression system 200 also includes a jacket 224. In the example, the jacket 224 is removably coupled to the bracket 214 and substantially surrounds the top surface 204, front surface 208, and bottom surface 206 of the body 202. In alternative examples, if the body includes an open top surface, the jacket 224 substantially surrounds the front surface and the bottom surface. FIGS. 2A-2C illustrate the jacket 224 in a deflated configuration, however, the jacket 224 may be actuated, via selective inflation, so that it may slide relative to the bottom surface 206 so as to pull breast tissue away from the chest wall and into the imaging area to obtain a desired breast compression profile. More specifically, the jacket 224 includes a first end 226 that is coupled to the top of the bracket 214 with one or more connection elements 228. For example, the connection element 228 may include an elongated slot 230 defined in the first end 226 such that a corresponding projection 232 of the bracket 214 is received therein. The elongated slot 230 enables the first end 226 to slide towards the front surface 208 while still being coupled to the bracket 214. This allows the jacket 224 to slide in relation to the body 202. In other examples, the first end 226 may include elastic material that enables the jacket 224 to slide in relation to the body 202. A second end 234 of the jacket 224 is coupled to the bottom of the bracket 214 with one or more connection elements 236. Unlike the first end 226, the second end 234 is secured to the bracket 214 such that the second end 234 does not move relative to the bracket 214.

The jacket 224 also includes at least one inflatable chamber 238 that is disposed below a recess 240 defined on the bottom of the bracket 214 and adjacent to the bottom surface 206. Each chamber of the inflatable chamber 238 may be selectively and/or independently inflated as described further below. Additionally, the jacket 224 includes a sheet 242 disposed below the bottom surface 206. The sheet 242 is positioned adjacent to the inflatable chamber 238 and separated by a heat-sealed seam 244. The inflatable chamber 238 is configured to selectively inflate into the recess 240 and pull on the first end 226 to slide the sheet 242 along the bottom surface 206 towards the bracket 214. This sliding movement of the sheet 242 pulls breast tissue away from the chest wall and into an imaging area and controls the profile of the breast, for example, a nipple profile position. The imaging area may be defined as an area below the compression paddle and above the imaging receptor and is depicted generally in FIG. 2C as element 245. With the inflatable chamber 238 below the bracket 214, the inflatable chamber 238 and the seam 244 are positioned outside of the imaging area of the imaging receptor so as to reduce and eliminate imaging artifacts.

In some examples, the sheet 242 includes one or more cushioning chambers 246 disposed below the bottom surface 206 and extending along at least a portion of the front surface 208. Each chamber of the cushioning chamber 246 may be selectively and/or independently inflated as described further below. The cushioning chamber 246 is configured to provide comfort to the patient during breast compression. For example, the cushioning chamber 246 may be an inflatable chamber that is controlled independent of the inflatable chamber 238. In an example, the cushioning chamber 246 is selectively inflatable to a lower pressure than the pressure in the inflatable chamber 238. The jacket 224 may be manufactured from a thin-film flexible material such as a polyurethane material that has a high tensile strength and limited stretching characteristics when surrounding the body 202. Additionally, the material is advantageously disposable. As such, after use with a first patient, the jacket 224 may be removed and a new jacket may be applied for a subsequent patient. This may reduce the need to clean or otherwise treat the surface of the breast compression system 200 between patients.

Figure 3:
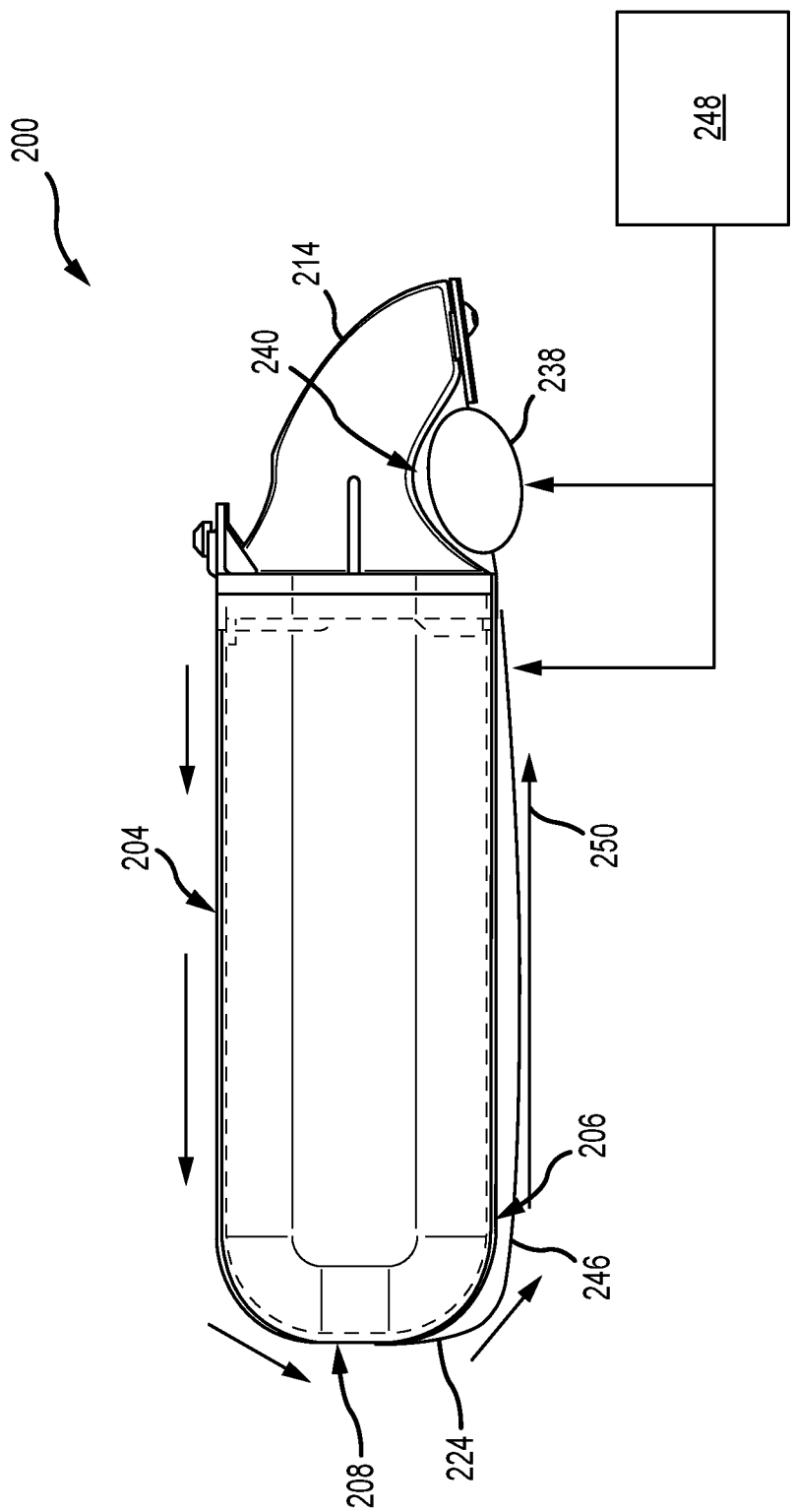
FIG. 3 is a schematic view of the breast compression system.

FIG. 3 is a schematic view of the breast compression system 200 in an inflated configuration. The jacket 224 may be coupled in flow communication to a fluid source 248 of the imaging system that is configured to deliver a flow of fluid to the jacket 224 and selectively inflate the inflatable chamber 238 and/or the cushioning chamber 246. The inflatable chamber 238 and the cushioning chamber 246 can be selectively inflated and, if desired, selectively deflated, to a pressure as required or desired via the fluid source 248. For example, the fluid may be air or any other gas or liquid that enables the jacket 224 to function as described herein. In operation, as the breast compression system 200 is compressing the patient's breast, the inflatable chamber 238 is being selectively inflated via the fluid source 248. The inflatable chamber 238 inflates and expands into the bracket recess 240. This inflation induces the sheet 242 to slide 250 along the bottom surface 206, and the sliding movement 250 of the jacket 224 pulls the breast tissue away from the chest wall so as to reduce a pulling sensation felt by the patient. In some examples, the inflation occurs substantially simultaneously with the compressing of the breast.

When the cushioning chamber 246 is used, the cushioning chamber 246 may be selectively inflated or deflated along with the inflatable chamber 238 so as to provide additional comfort for the patient and further reduce the pulling sensation. In some examples, the cushioning chamber 246 is inflated to a lower pressure than that of the inflatable chamber 238 because too much pressure of the cushioning chamber 246 may push breast tissue out from the imaging area. In other examples, the inflation of the cushioning chamber 246 is independently controlled from the inflation of the inflatable chamber 238. After the simultaneous inflation of the inflatable chamber 238 and the cushioning chamber 246, the inflatable chamber 238 and/or the cushioning chamber may further be selectively inflated or deflated to adjust the profile of the breast and/or nipple if desired. In yet other examples, after the breast is compressed, the cushioning chamber 246 is only then selectively inflated or deflated.

Figure 4A:
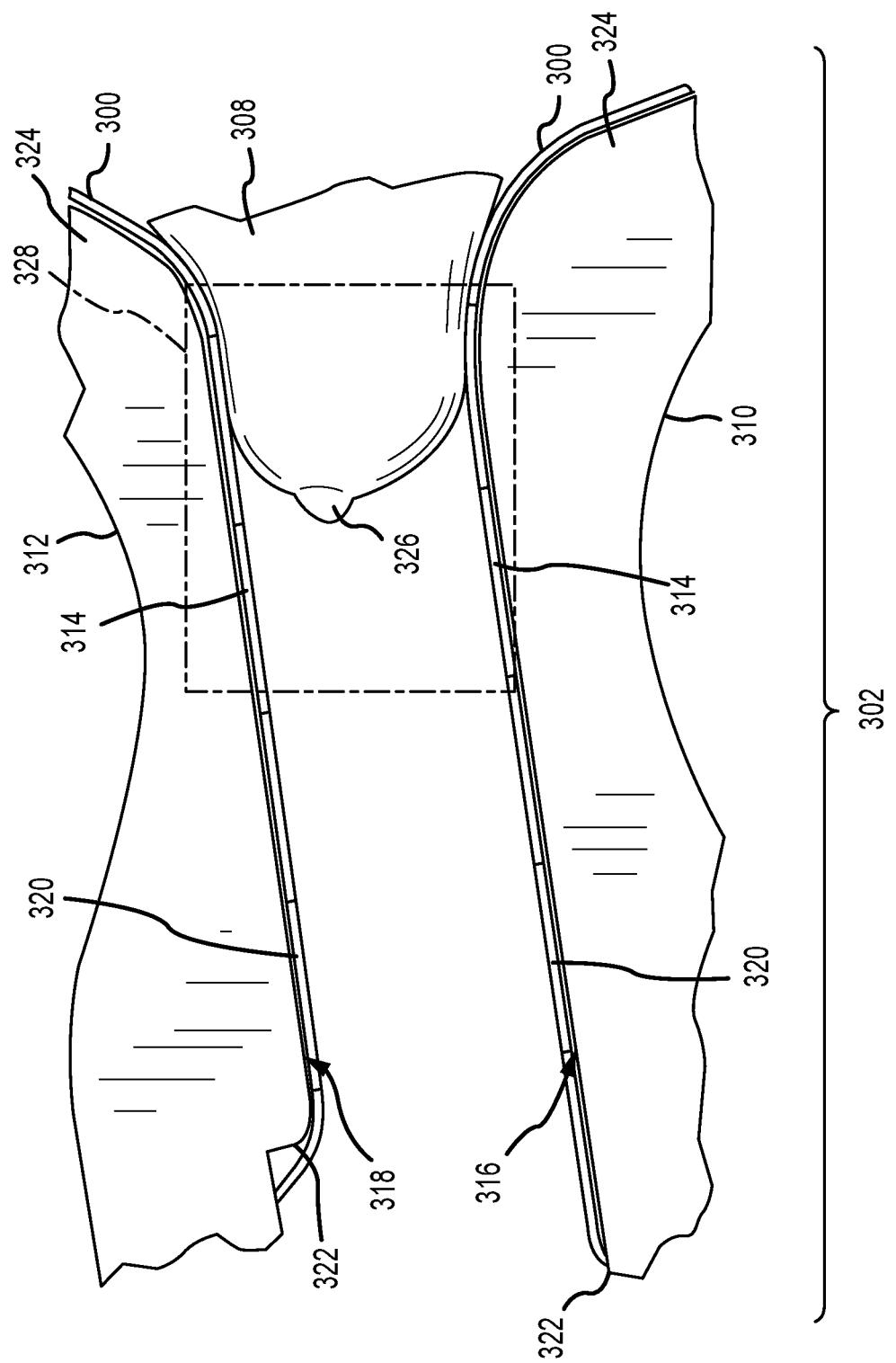
FIGS. 4A-4C are schematic side views of an exemplary inflatable jacket in a deflated condition, a first inflated condition, and a second inflated condition, respectively.
Figure 4B:
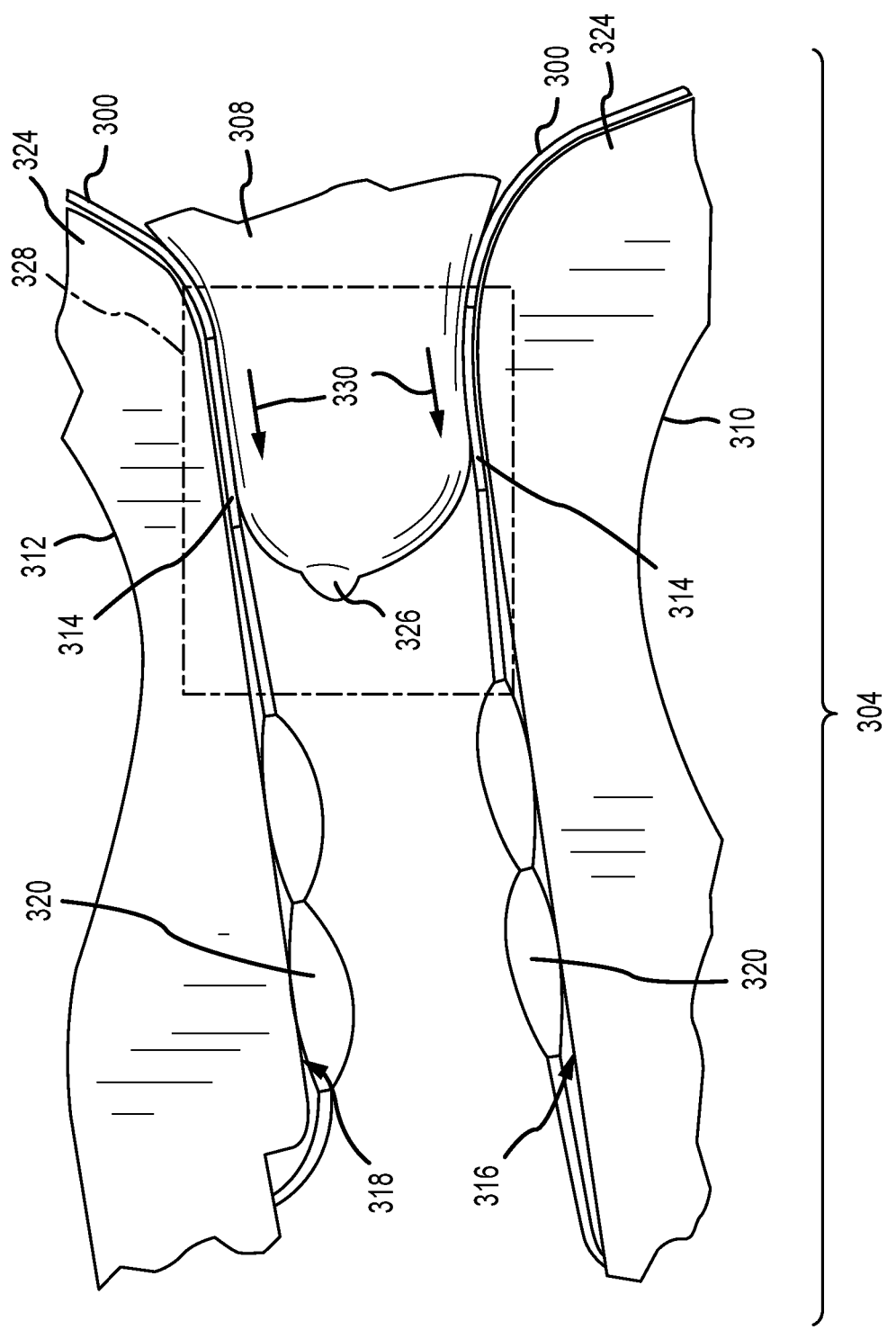
Figure 4C:
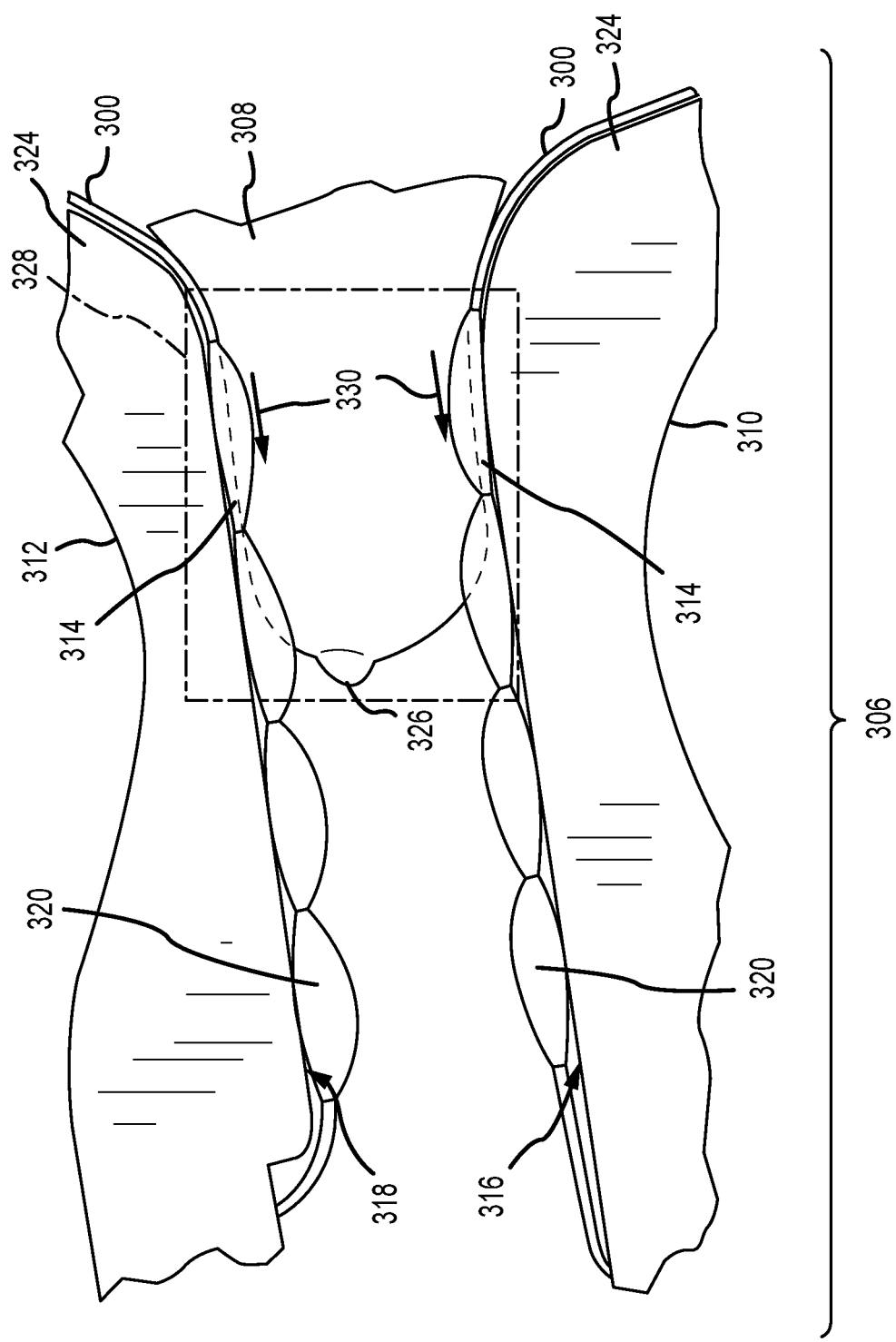

FIGS. 4A-4C are schematic side views of an exemplary inflatable jacket 300 in a deflated condition 302, a first inflated condition 304, and a second inflated condition 306, respectively. Referring concurrently to FIGS. 4A-4C, a patient's breast 308 is positioned between a breast support platform 310 and a compression paddle 312 that both include inflatable jackets 300. The jacket 300 includes a plurality of cushioning chambers 314 positioned over and at least partially cover compression surfaces 316 and 318 of the breast support platform 310 and the compression paddle 312, respectively. The jacket 300 also includes a plurality of inflatable chambers 320 adjacent to the compression surface 316, 318. In the example, the jacket 300 on the platform 310 is similar to the jacket 300 on the paddle 312. In alternative examples, the jackets 300 may be different on the platform 310 and the paddle 312. The inflatable chambers 320 are positioned adjacent to a bracket end 322 of the compression surfaces 316, 318 while the cushioning chambers 314 are positioned adjacent to a front surface 324 of the compression surfaces 316, 318 and in contact with the breast 308. In the example, the compression paddle 312 has an open top surface and the bracket end 322 is integral with the compression surface 318 and the front surface 324.

Referring to FIG. 4A, the patient's breast 308 is positioned on the breast support platform 310, and the compression paddle 312 is located above the breast 308 so as to restrict movement. The jackets 300 cover both compression surfaces 316, 318, and the cushioning chambers 314 and the inflatable chambers 320 are deflated before compression begins. For imaging, it is desirable to pull breast tissue away from the chest wall and control the profile of the breast 308 (e.g., nipple region 326 position). As such, the health professional may manually manipulate the profile of the breast 308 before compressing the breast. However, during compression, in the absence of the inflatable jacket 300, breast tissue may be pushed towards the chest wall and the nipple region 326 may move and roll so as to change the profile of the breast 308.

Accordingly, as the compression paddle 312 is moved toward the platform 310 and compresses the breast 308, each jacket 300 is selectively inflated so as to pull breast tissue away from the chest wall and into an imaging area 328 and control the profile of the breast 308. Turning to FIG. 4B, in the first inflated position 304, the inflatable chambers 320 begin to inflate by receiving a flow of fluid. When the inflatable chambers 320 selectively inflate, the jacket 300 slides along the compression surfaces 316, 316 and away from the chest wall as illustrated by arrows 330. As such, breast tissue is pulled further into the imaging area 328. Additionally, the nipple region 326 profile is maintained so it does not roll or fold in undesirable directions (e.g., the nipple region rolling in a downward direction). In some examples, by substantially simultaneously compressing the breast 308 and pulling breast tissue away from the front surfaces 324, any pulling sensation experienced by the patient is reduced. In this example, the inflatable chambers 320 in each jacket 300 are selectively inflated at approximately the same rate and at the same time so as to act in concert and slide the jacket 300 along the compression surfaces 316, 318. In alternative examples, the inflatable chambers 320 in a single jacket 300 or in each jacket 300 may be independent chambers and selectively inflate at different rates and/or time sequences. Additionally, by using multiple inflatable chambers, the left and right edges of the jacket 300 do not pull as far into the image area 328 when the chambers are inflated. When large chambers are inflated, the middle section tends to rise, while the end sections tend to draw inwards and into the imaging area.

Referring to FIG. 4C, the breast 308 is compressed and the inflatable chambers 320 are inflated so that breast tissue is pulled into the imaging area 328 and the nipple region 326 profile is maintained. Additionally, after breast compression, the cushioning chambers 314 may be selectively inflated or deflated so as to increase comfort of the patient and to reduce wrinkling of the breast tissue. The cushioning chambers 314 can be inflated to a lower pressure so as to not push breast tissue towards the chest wall and out of the imaging area 328. In the example, the inflation pressure of the inflatable chambers 320 is greater than the inflation pressure of the cushioning chambers 314. In alternative examples, these inflation pressures may be equal or the cushioning chambers 314 greater than the inflatable chambers 320.

Additionally, in some examples, the cushioning chambers 314 may inflate in concert with the inflatable chambers 320 during the breast compression and then be selectively adjusted after the breast compression. Alternatively, in other examples, breast compression may begin without inflation of the jacket 300 up to a predetermined compression value, and then the jacket 300 may be selectively inflated before finishing breast compression to the final compression value.

Figure 5:
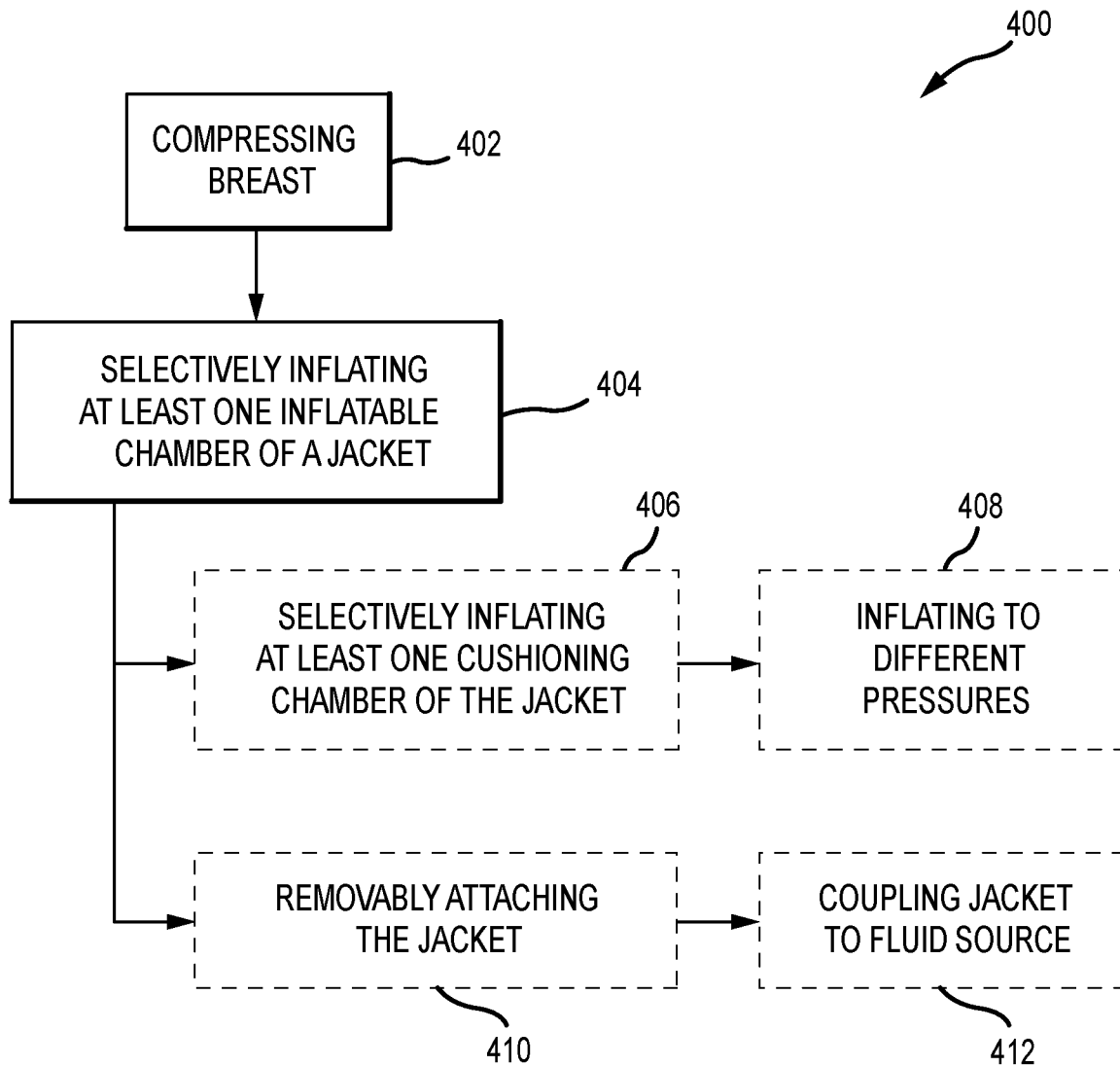
FIG. 5 is a flowchart of a method for compressing a breast in an imaging system.

FIG. 5 is a flowchart of a method 400 for compressing a breast in an imaging system. In this example, the imaging system includes a jacket having at least one inflatable chamber and a sheet. The method includes compressing a breast between a compression paddle and a platform (operation 402). The at least one inflatable chamber of the jacket disposed on the breast compression paddle is selectively inflated such that the sheet slides along a compression surface and pulls at least some breast tissue away from a patient's chest wall and into an imaging area (operation 404).

Additionally, the sheet may include at least one cushioning chamber disposed below the compression surface, so that the method 400 further includes after the breast is compressed between the compression paddle and the platform, selectively inflating the at least one cushioning chamber (operation 406). The at least one inflatable chamber can be inflated to a different pressure than a pressure of the at least one cushioning chamber (operation 408). The method 400 may also include removably attaching the jacket on the breast compression paddle (operation 410), and coupling in fluid communication the jacket to a fluid source (operation 412).

Figure 6A:
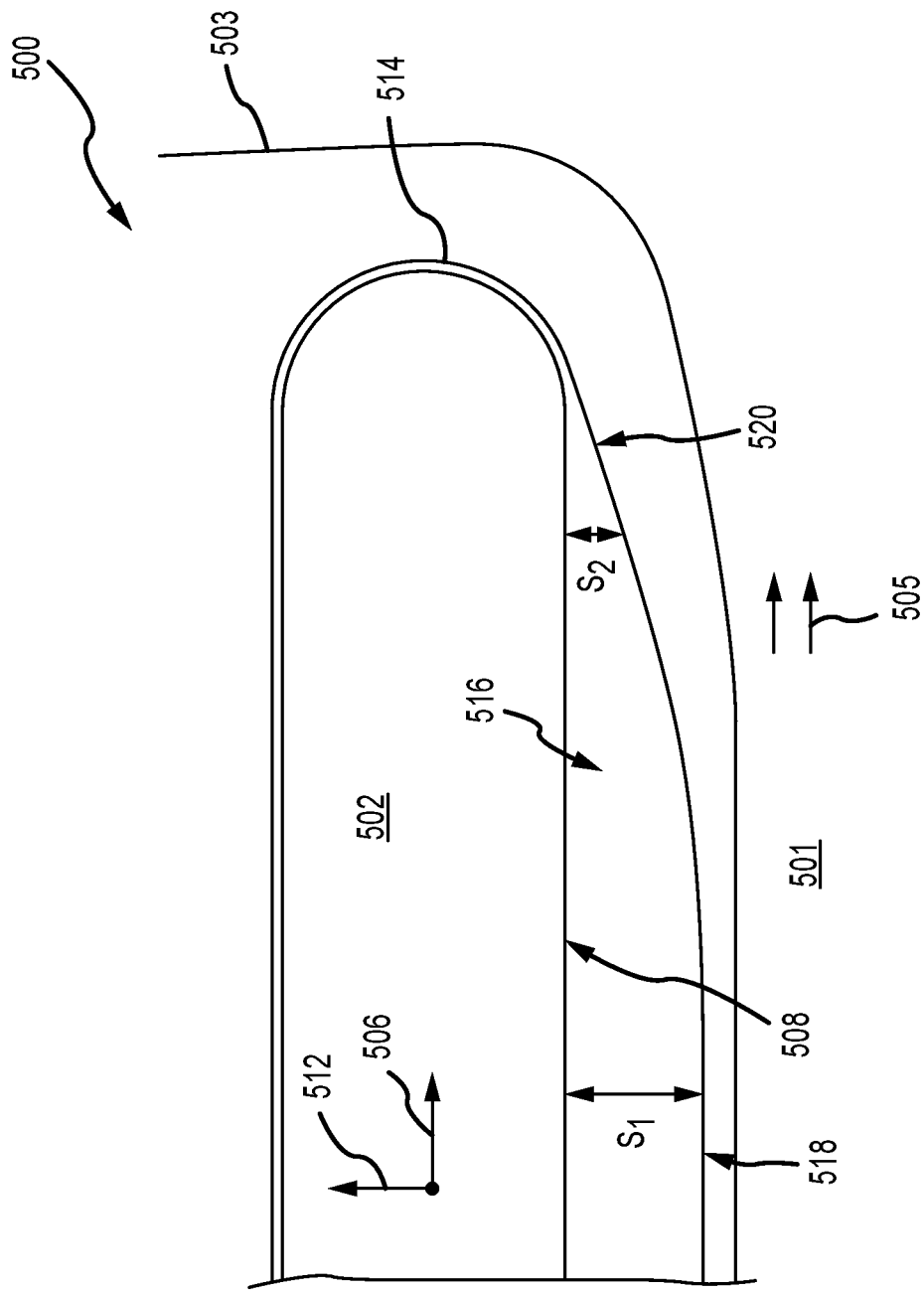
FIGS. 6A and 6B are side views of another breast compression system.
Figure 6B:
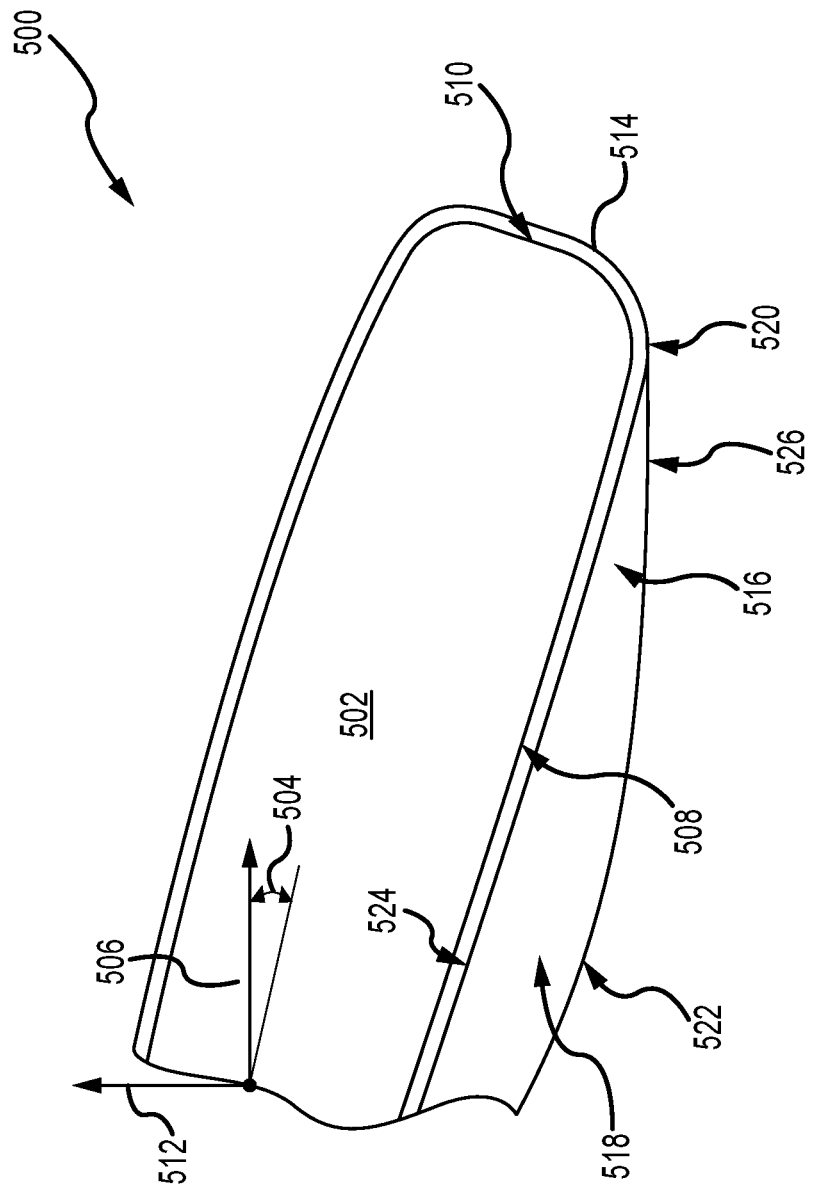

FIGS. 6A and 6B are side views of another breast compression system 500. With reference first to FIG. 6A, a compression paddle 502 and/or the platform (not shown) are supported such that they extend substantially horizontally 506 from the support arm (not shown for clarity). This provides for a generally flat bottom surface 508 for breast 501 compression therebetween. However, when an inflatable jacket 514 is coupled to the compression paddle 502, an inflatable chamber 516 inflates proximate a central area 518 of the inflatable jacket 514. This ballooning effect causes a greater separation S₁ between the central area 518 of the jacket 514 and the compression paddle 502, with less separation S₂ between an edge section 520 of the jacket 514 and the compression paddle 502. This may push breast tissue out along the edge sections 520 of the inflatable jacket 514. When the edge sections 520 are adjacent to the front of the patient's breast (e.g., the nipple region) or the sides of the patient's breast, the balloon effect further assists in flattening the breast 501 during compression procedures. However, at the chest wall edge, the balloon effect may push breast tissue towards the chest wall 503 as illustrated by arrows 505, which is undesirable for imaging. As such and now with reference to FIG. 6B, to reduce the balloon effect along the chest wall, the compression paddle 502 of the breast compression system 500 is positioned at an angle 504 relative to the horizontal axis 506.

Similar to the examples described above, the compression paddle 502 includes the bottom surface 508 and a front surface 510. The compression paddle 502 can be coupled to a support arm by a bracket (not shown) and the support arm generally extends along a vertical axis 512 that is substantially orthogonal to the horizontal axis 506. Additionally, the inflatable jacket 514 can be coupled to the compression paddle 502 and adjacent to the bottom surface 508 and the front surface 510. In examples, the jacket 514 may be at least partially disposed around the compression paddle 502. In this example, the inflatable jacket 514 includes at least one inflation chamber 516 that is proximate the bottom surface 508 that is angled relative to the horizontal axis 506. As illustrated in FIG. 6B, the entire compression paddle 502 is angled and the bracket can define the extension angle from the support arm. As such, the bottom surface 508 is substantially planar. In other examples, the compression paddle 502 may have a bottom surface 508 that has at least one curve defined therein such that the front surface 510 is positioned at an angle.

The inflation chamber 516 is configured to selectively inflate (e.g., through a flow of compressed air or any other fluid) to provide cushioning to the patient's breast and/or to provide further compressive force to the breast. When the inflation chamber 516 is inflated, the central area 518 of the chamber 516 expands more than the edge sections 520. This ballooning effect generates a substantially domed-shaped outer surface 522 of the inflation chamber 516, while an inner surface 524 of the inflation chamber 516 remains substantially flat due to the bottom surface 508 of the compression paddle 502. The domed-shaped outer surface 522 forms a sloped or tapered edge section 526 that is proximate the edge 520. In this example, the compression paddle 502 is angled 504 such that the sloped section 524 is oriented substantially parallel to the horizontal axis 506.

By angling the compression paddle 502 in a downward direction towards the patient's chest wall, the ballooning effect of the inflation chamber 516 along the patient's chest wall is reduced or eliminated. That is, the angled compression paddle 502 orients the sloped section 524 of the inflation chamber 516 substantially parallel to the support platform so that breast compression along the chest wall is substantially along the vertical axis 512 and pushing of breast tissue towards the chest wall is reduced or eliminated. This pulls as much breast tissue as possible is pulled into the imaging area of the x-ray system and maintains a more desirable breast compression profile to increase imaging efficiencies.

Figure 7:
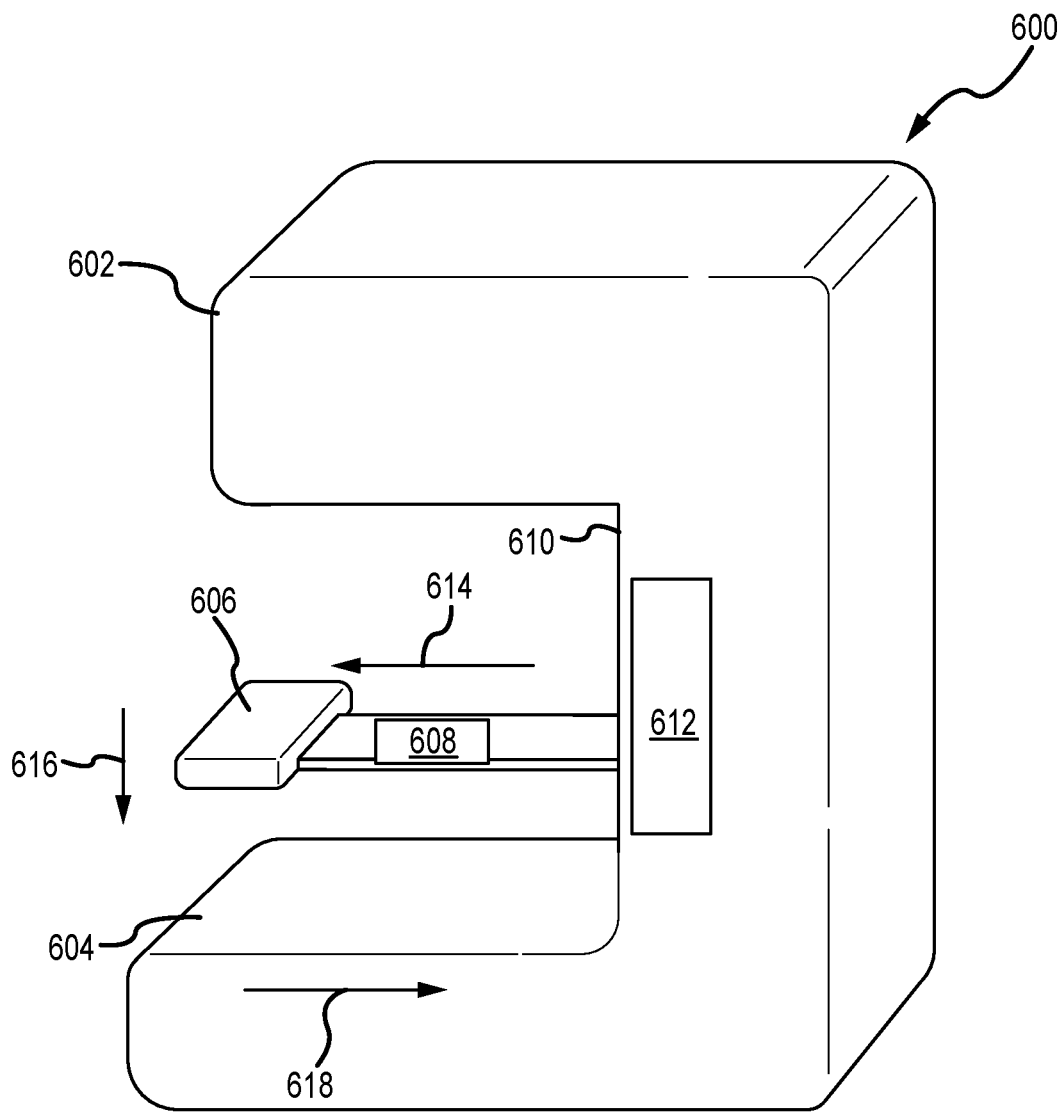
FIG. 7 is a schematic view of another imaging system.

FIG. 7 is a schematic view of another imaging system 600. Similar to the example described above in FIGS. 1A and 1B, the imaging system 600 includes an x-ray tube head 602 and a support platform 604. Additionally, a compression paddle 606 is disposed between the x-ray tube head 602 and the support platform 604. The compression paddle 606 is configured to immobilize a patient's breast against the support platform 604 for x-ray imaging. In the examples of FIGS. 2A-5, to maintain a more desirable breast profile for imaging and prevent rolling or folding of breast tissue, an inflatable jacket can be used. In the example of FIG. 7, however, an extension/retraction drive system 608 is coupled to the compression paddle 606 to mechanically pull breast tissue away from the chest wall and into the imaging area during the compression procedure. The extension/retraction drive system 608 may be any type of electromechanical system that enables movement of the compression paddle as described herein. For example, the drive system 608 may be a geared system, a pulley system, or a combination thereof. In other examples, the drive system 608 may be a piston movement system or a solenoid actuator.

A support arm 610, which supports the platform 604 and the compression paddle 606, houses a vertical drive system 612 that is coupled to the paddle 606. The vertical drive system 612 is configured to move compression paddle 606 towards the support platform 604 and compress the patient's breast for imaging. This vertical movement defines a first axis that is substantially orthogonal to the compression surface of the support platform 604. Additionally, the compression paddle 606 is coupled to the extension/retraction drive system 608 such that the paddle 606 also can be extended and/or reacted with respect to the support arm 610. This horizontal movement defines a second axis that is substantially parallel to the compression surface of the support platform 604. Accordingly, during a breast compression procedure, the compression paddle 606 may be extended 614 away from the support arm 610 along the first axis before moving 616 the compression paddle 606 towards the support platform 604 along the second axis. Then, as the compression paddle 606 is compressing the patient's breast, the compression paddle 606 may be retracted 618 towards the support arm 610 along the first axis to draw breast tissue away from the chest wall of the patient. The compression movement 616 and the retraction movement 618 of the compression paddle 606 may occur substantially simultaneously. In other examples, the compression movement 616 and the retraction movement 618 may be discrete movements that occur individually.

By mechanically pulling breast tissue away from the chest wall and into the imaging area via the compression paddle 606 and the drive systems 608, 612, the system 600 reduces rolling and folding of breast tissue so as to maintain a more desirable breast profile and increase imaging efficiencies. Additionally, by substantially simultaneously compressing and pulling the patient's breast, the drive systems 608, 612 enables the pulling sensation experienced by the patient to be reduced, thereby increasing patient comfort.

Figure 8:
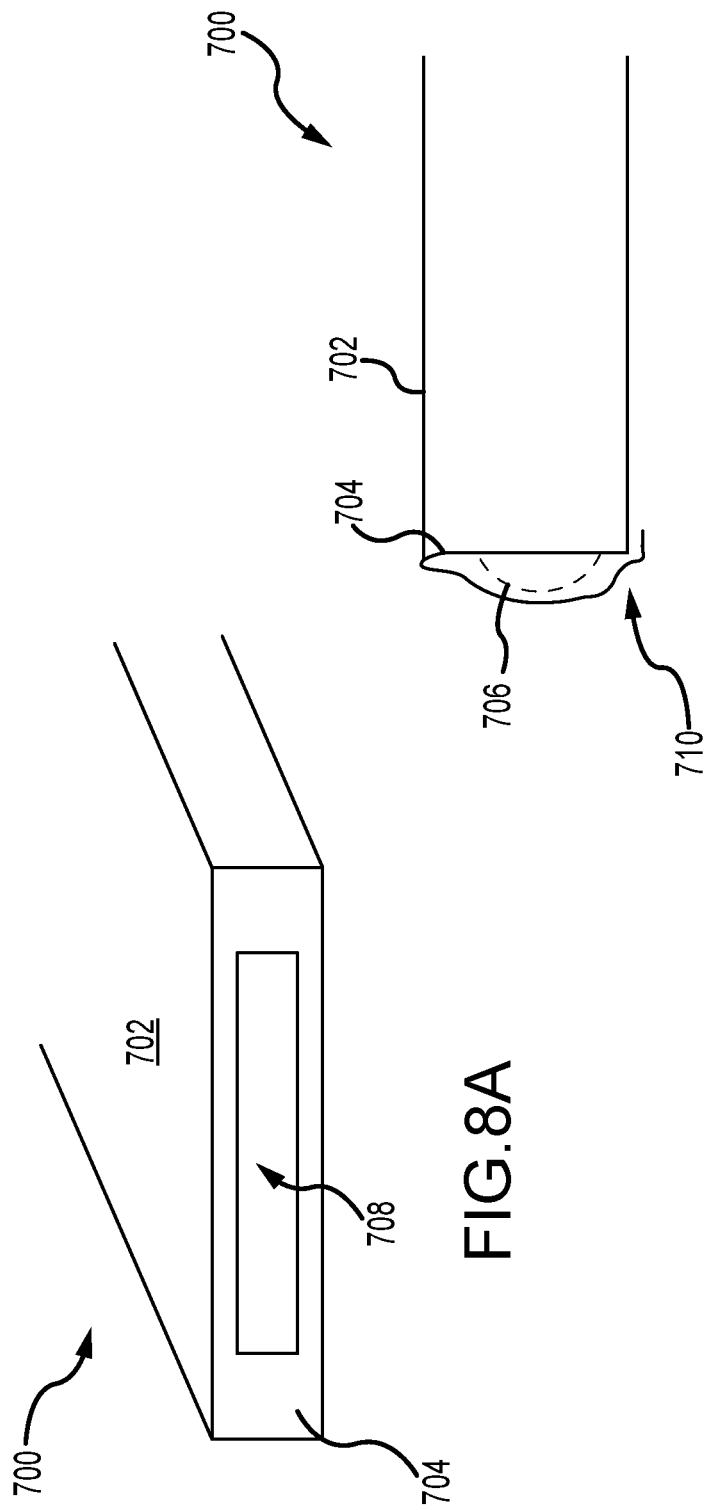
FIGS. 8A and 8B are a perspective view and a side view, respectively, of a support platform.

FIGS. 8A and 8B are a perspective view and a side view, respectively, of a support platform 700. Referring concurrently to FIGS. 8A and 8B and as described above, the support platform 700 includes a top compression surface 702 to facilitate breast compression. The support platform 700 also houses the image receptor and tilting mechanism (not shown). During breast compression and imaging procedures, the patient is positioned such that the chest wall is pressed against a front surface 704 of the support platform. The front surface 704 is typically disposed at an angle (e.g., a 90° angle) to the compression surface 702. This position may cause some discomfort for the patient, as the support platform 700 is typically a hard rigid plastic housing. As such, in this example, the support platform 700 includes an inflatable membrane 706 disposed along the front surface 704. The inflatable membrane 706 is configured to selectively inflate and provide a cushioned surface on the support platform 700 such that the patient is more comfortable during the compression and imaging procedures.

A recess 708 is defined in the front surface 704 of the support platform 700 such that the inflatable membrane 706 can be disposed along the front surface 704. In other examples, the recess 708 can be a cutout, opening, slot, etc. as required or desired. This position enables the image receptor and tilting mechanism to maintain a clearance fit within the support platform 700 and positions the inflatable membrane 706 out of the imaging area such that no image artifacts are formed. When inflated, the inflatable membrane 706 extends out from the front surface 704 such that a cushion is provided for the patient. When the inflatable membrane 706 is not inflated, the inflatable membrane 706 can retract within the support platform 700. A flexible cover 710 may be positioned over the front surface 704 and the inflatable membrane 706 and is configured to expand and retract with the inflation of the inflatable membrane 706. The flexible cover 710 may be removable and/or disposable so that the support platform 700 can be easily cleaned and disinfected before patient use. In other examples, the inflatable membrane 706 may be exposed to patient contact and configured to be cleaned with disinfectant between patients.

In operation, the inflatable membrane 706 may be coupled in fluid communication to a fluid control unit such that during the compression procedure the inflatable membrane 706 is inflated to provide a cushioned element on the support platform 700. The inflatable membrane 706 may be filled to a predetermined pressure for every compression procedure or may be filled to varying pressure based on the imaging procedure or patient comfort level. By providing a cushioned surface on the support platform 700 that can easily be cleaned and re-pressurized, the technologist no longer has to work with foam pads that may be difficult to clean. Additionally, a heated fluid may be channeled to the inflatable membrane 706 such that the support platform 700 is at least partially heated for patient comfort. The fluid that is channeled to the inflatable membrane 706 can be a liquid, such as water and the like, or may be a gas, such as air and the like. In alternative examples, any other fluid or fluid compound may be used as required or desired.

In other embodiments, the inflatable membrane 706 may be combined with the flexible cover 710 as a removable inflatable jacket. The jacket may be coupled to a fluid source such that the inflatable membrane 706 can fill with fluid and expand. In this example, the front surface 704 of the support platform 700 is flat such that the inflatable membrane 706 can inflate and extend away from the front surface 704 and provide a cushioned surface on the support platform 700 as described herein. By using the inflatable jacket, after a compression and imaging procedure, the jacket can be disposed of so as to facilitate an easy and quick cleaning of the image system between patients.

The inflatable membrane 706 described herein enables a cushioned support to be positioned on the support platform 700 for increasing overall patient comfort during breast compression and imaging procedures. For example, the cushion enables the patient to be in the compressed position for longer periods of time and with test movement to increase efficiency of the compression and imaging procedure. The inflatable member 706 is positioned on the front wall of the support platform 700 so that a cushion is provided at the chest wall of the patient and without introducing image artifacts into the imaging area. The inflatable member 706 can be selectively inflated based on patient needs and desires. Furthermore, the inflatable member 706 may receive a heated fluid flow to further increase patient comfort during breast compression and imaging procedures.

Figure 9:
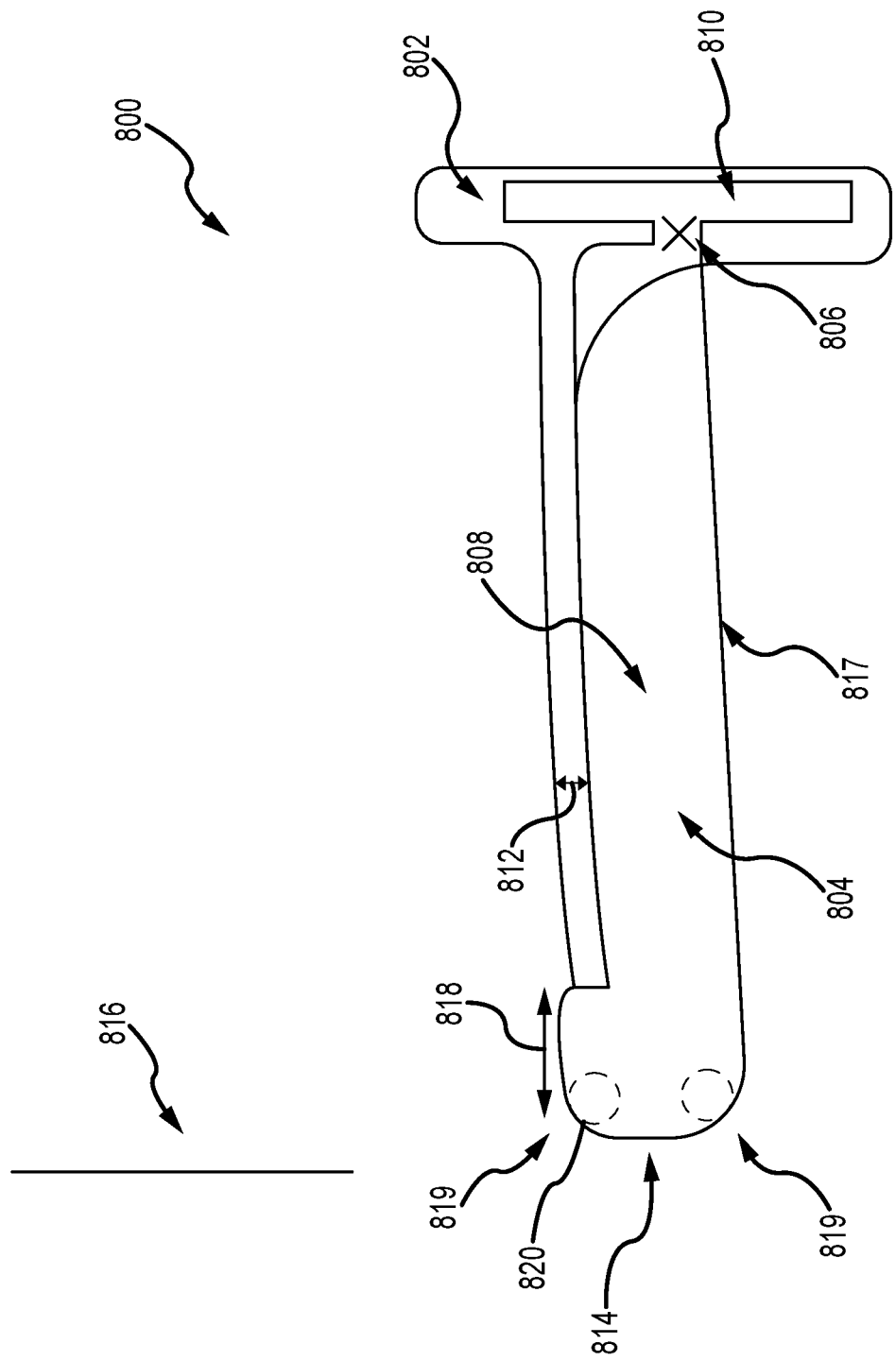
FIG. 9 is a side view of a breast compression paddle.
Figure 10B:
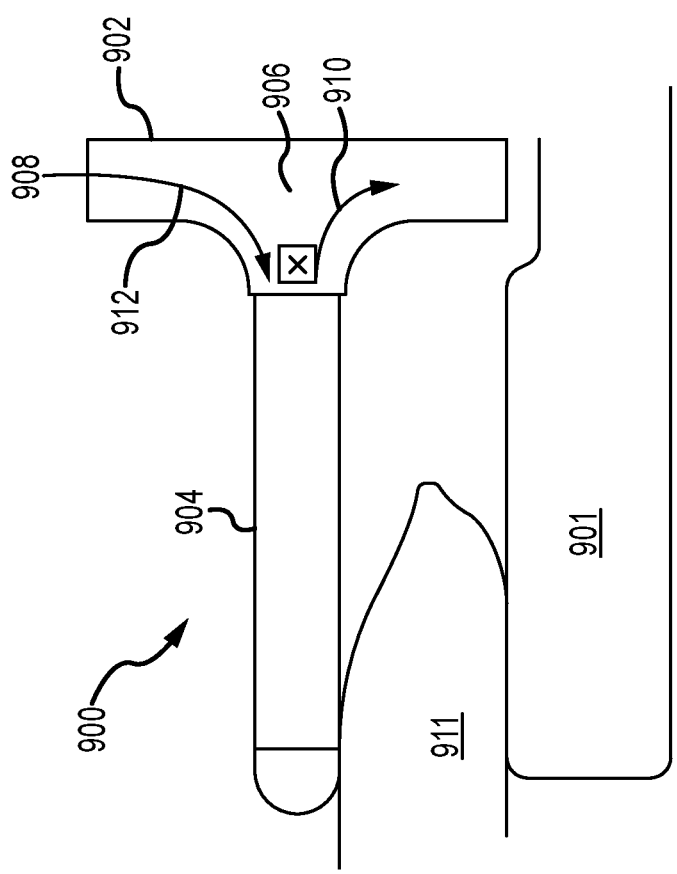
FIGS. 10A-10D are a perspective view, a side cross-sectional view, a top view, and a front view, respectively, of another breast compression paddle.
Figure 10A:
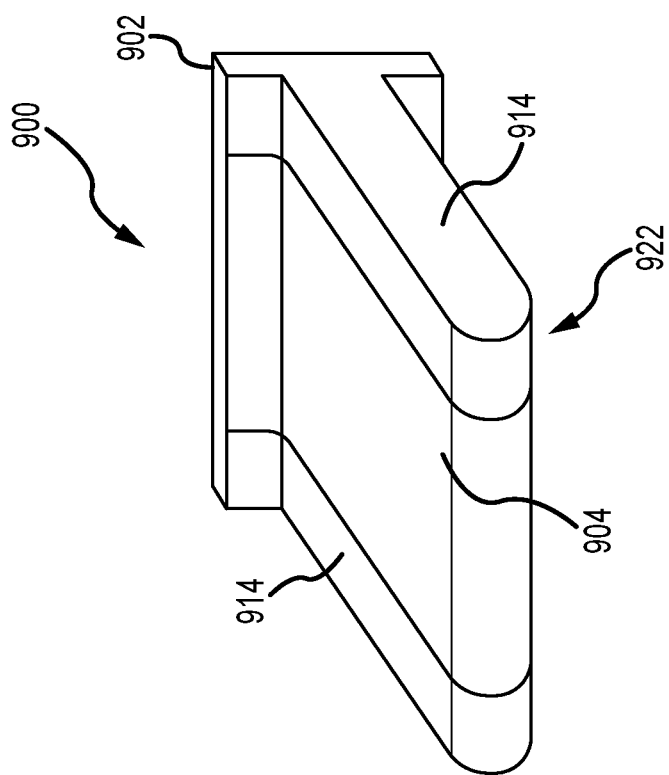
Figure 10D:
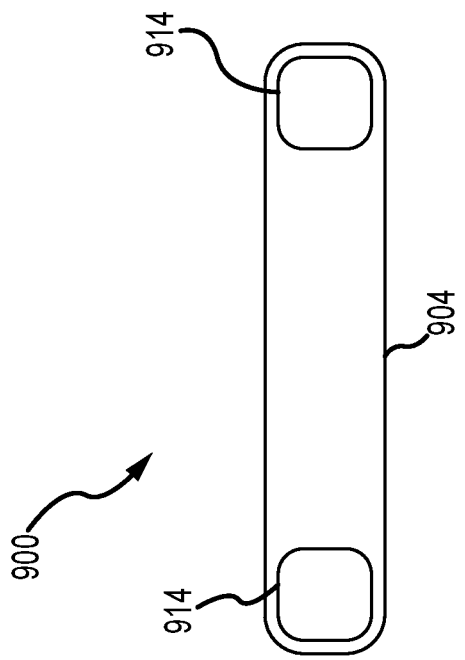
Figure 10C:
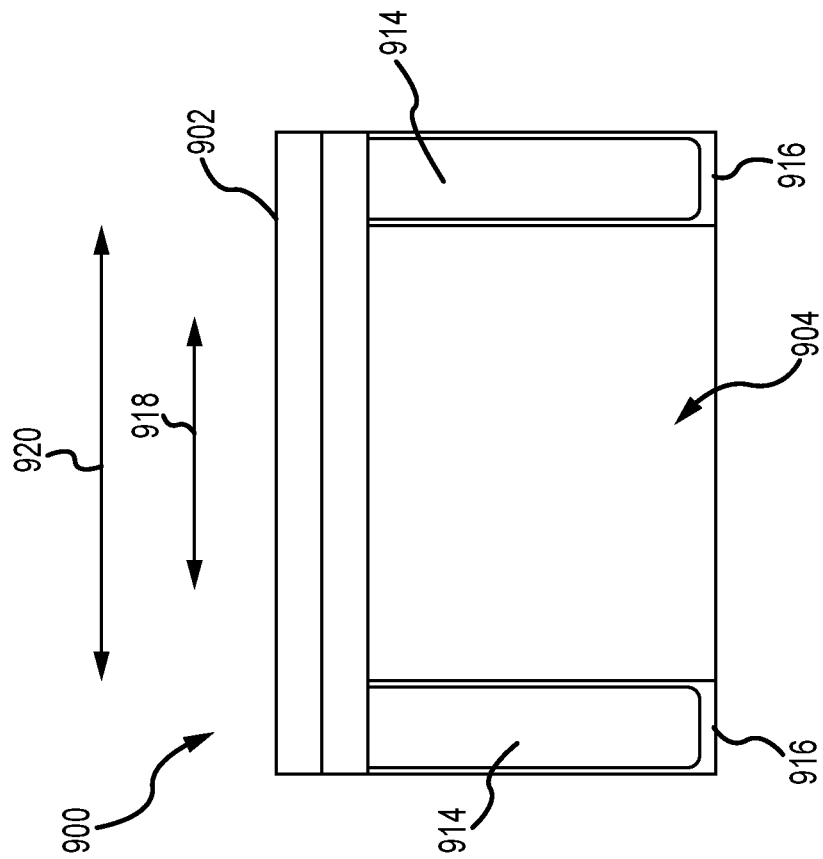

FIG. 9 is a side view of a breast compression element 800. As described above, the imaging technologist typically adjusts the patient's breast within the compression unit while moving the compression paddle towards the support platform. This compression of the patient's breast generally must be done with sufficient force to immobilize the breast and to spread out the breast tissue for x-ray imaging, and as such, over-compression may occur, which increases patient discomfort and anxiety during the imaging procedure. Accordingly, the breast compression element 800 described below may be used with the imaging systems described herein to provide increased comfort to the patent, while still enabling for sufficient immobilization and shaping of the patient's breast.

In this example, the compression element 800 includes a structural support 802 and an inflatable bladder 804 coupled thereto. The structural support 802 is formed from a rigid, radiotranslucent material that can be removably coupled to the compression assembly. On the bottom side (e.g., forming the bottom surface of the support 802), the inflatable bladder 804 is positioned. The inflatable bladder 804 is configured to receive and store a fluid, such that the inflatable bladder 804 can be pressurized to a predetermined pressure. Additionally, a bleed valve 806 is in fluid communication with the inflatable bladder 804. The bleed valve 806 is configured to selectively de-pressurize and release fluid from the inflatable bladder 804 as required or desired such that over-compression of the patient's breast may be reduced or eliminated.

In one example of operation, the inflatable bladder 804 may be initially filled with a fluid 808 such that the inflatable bladder 804 is formed to an inflated shape and/or pressure. As the compression element 800 moves towards the support platform and compresses the patient's breast, the rigid structural support 802 generates a compressive force on the breast. The bleed valve 806 selectively releases fluid 808 from the inflatable bladder 804. The bleed valve 806 is configured to at least partially open when the fluid pressure in the inflatable bladder 804 reaches a predetermined value. Additionally or alternatively, the bleed rate of the valve 806 may be controllable so as to define the fluid pressure within the inflatable bladder 804. Thus, the compressive force applied to the patient breast by the structural support 802 can be at least partially dissipated by the inflatable bladder 804 and fluid 808 configuration. This enables the technologist to apply compression force sufficient to immobilize and compress the breast without over-compressing and causing unnecessary discomfort. In this way, the inflatable bladder 804 acts as a cushioning component disposed between the patient's breast and the structural support 802 that at least partially defines a compression load to be applied to the breast. The inflatable bladder 804 may receive a reload charge of fluid 808 between patients. The inflatable bladder 804 may be manufactured from a silicon-based, vinyl-based, or like material that is radiotranslucent and can be easily cleaned and/or disinfected.

In some examples, the fluid 808 may be air or an equivalent gas that can be discharged to the atmosphere by the bleed valve 806. The bleed valve 806 may include a muffler or any other type of device that reduces or eliminates the sound of the air exiting out of the bleed valve 806. In other examples, an exit tube (not shown) may extend from the bleed valve 806 so as to channel the air to a remote discharge location away from the patient. In further examples, a reservoir 810 may be coupled in flow communication with the inflatable bladder 804 and on the opposite side of the bleed valve 806 so as to receive the discharged fluid 808. In this example, the bleed valve 806 may be a two-way valve such that the fluid 808 can be introduced to and removed from the inflatable bladder 804. The reservoir 810 may be defined at least partially within the structural support 802, as illustrated in FIG. 9, or may be remote from the compression element 800 and coupled together via one or more tubes. In still other examples, the fluid 808 may be water or an equivalent liquid as required or desired, although post-imaging image processing would be acquired to address attenuation. The fluid 808 may also be heated so that the inflatable bladder 804 is warm and more calming for the patient.

Since both the structural support 802 and the inflatable bladder 804 are used to compress the patient's breast, the structural support 802 may have a thickness 812 that is thinner than a typical compression paddle. This reduced thickness enables for a lower amount of x-ray energy to be used for imaging since there is less penetrable structure for the x-rays. Additionally, in this example, a front wall 814 of the compression element 800 is formed entirely by the inflatable bladder 804, which provides cushioning at the chest wall 816 of the patient, and a compression surface 817 is formed by the inflatable bladder 804. The structural support 802 is offset 818 from the front wall 814 such that the inflatable bladder 804 fills the space. Furthermore, the inflatable bladder 804 may define one or more radii 819 along the front wall 814 such that the compression element 800 has smooth edges that are positioned adjacent the chest wall 816 to further provide cushioning and patient comfort. The radius 819 may be formed by the shape and/or size of the inflatable bladder 804, or may be at least partially defined by one or more support tubes 820 disposed within the inflatable bladder 804 so as to give shape and/or structure to the flexible bladder 804.

In another example of operation, the inflatable bladder 804 may not be initially filled, or only partially filled, with the fluid 808. In this configuration, the compression element 800 is moved towards the support platform and compresses the patient's breast, via the structural support 802, to an initial compression force. Once this initial compression force is reached, then fluid 808 may be introduced into the inflatable bladder 804 so as to increase the pressurization of the bladder 804 and further compress the patient's breast until a final compression force is reached. This operation can also reduce over-compression of the breast because the compression element 800 is not moved in relation to the support platform in order obtain the final breast compression force. In some examples, the inflatable bladder 804 may be coupled to the structural support 802 such that a single compression element 800 component is formed. In other examples, the inflatable bladder 804 may be removably attached to the structural support 802 so that inflatable bladder 804 is a disposable component. In that case, a new inflatable bladder 804 may be attached for each patient.

FIGS. 10A-10D are a perspective view, a side cross-sectional view, a top view, and a front view, respectively, of another breast compression element 900. Referring concurrently to FIGS. 10A-10D, the breast compression element 900 is disposed above a support platform 901 and includes a structural support 902 and an inflatable bladder 904. Similar to the examples described above, the inflatable bladder 904 is coupled to a bleed valve 906 such that a fluid 908 (e.g., air) can be exhausted to the atmosphere via an outlet 910 and control over-compression of the breast 911. Additionally, the inflatable bladder 904 includes an inlet 912 so that fluid 908 may be introduced into the bladder 904. However, in this example, the structural support 902 includes two substantially parallel arms 914 that are spaced apart from each other. The inflatable bladder 904 may be formed as a sheet with two end chambers 916 that can receive the arm 914 so as to removably couple the inflatable bladder 904 to the arms 914. This enables the inflatable bladder 904 to be formed as a sterile and disposable component.

In this example, it may be desirable that the inflatable bladder 904 be in tension between the arms 914 so that a compressive load can be applied to the breast 911. As such, the arms 914 should be sufficiently rigid (e.g., carbon fiber, aluminum, or the like), and may also be moveable towards and away from one another. For example, the arms 914 can move towards each other and towards a first distance 918 that enables the inflatable bladder 904, through the chambers 916, to be more easily attached to the structural support 902 and without tensioning the bladder 904. Once the inflatable bladder 904 is coupled to the arms 914, the arms 914 may be moved away from each other and to a second distance 920, so that tension is induced into the bladder 904. In some examples, the free end of the arm 914 may be formed with a radius feature 922 so that a radius of curvature can be defined in the inflatable bladder 904 such that the compression element 900 has smooth edges that are positioned adjacent the chest wall of the patient to further provide cushioning and patient comfort.

In operation, the compression element 900 may use the inflatable bladder 904 to release air pressure during the patient's breast compression, or may induce air into the inflatable bladder 904 during the compression procedures. Regardless, the compression element 900 reduces over-compression of the breast and increased patient comfort. Additionally, the structural support 902 and arm 914 may be positioned so as to not be in the imaging area of the imaging unit so that image artifacts are not formed. Furthermore, because the inflatable bladder 904 is the only component in the imaging area, lower x-ray energy may be used during imaging since there is no support structure to attenuate the x-rays.

Figure 11:
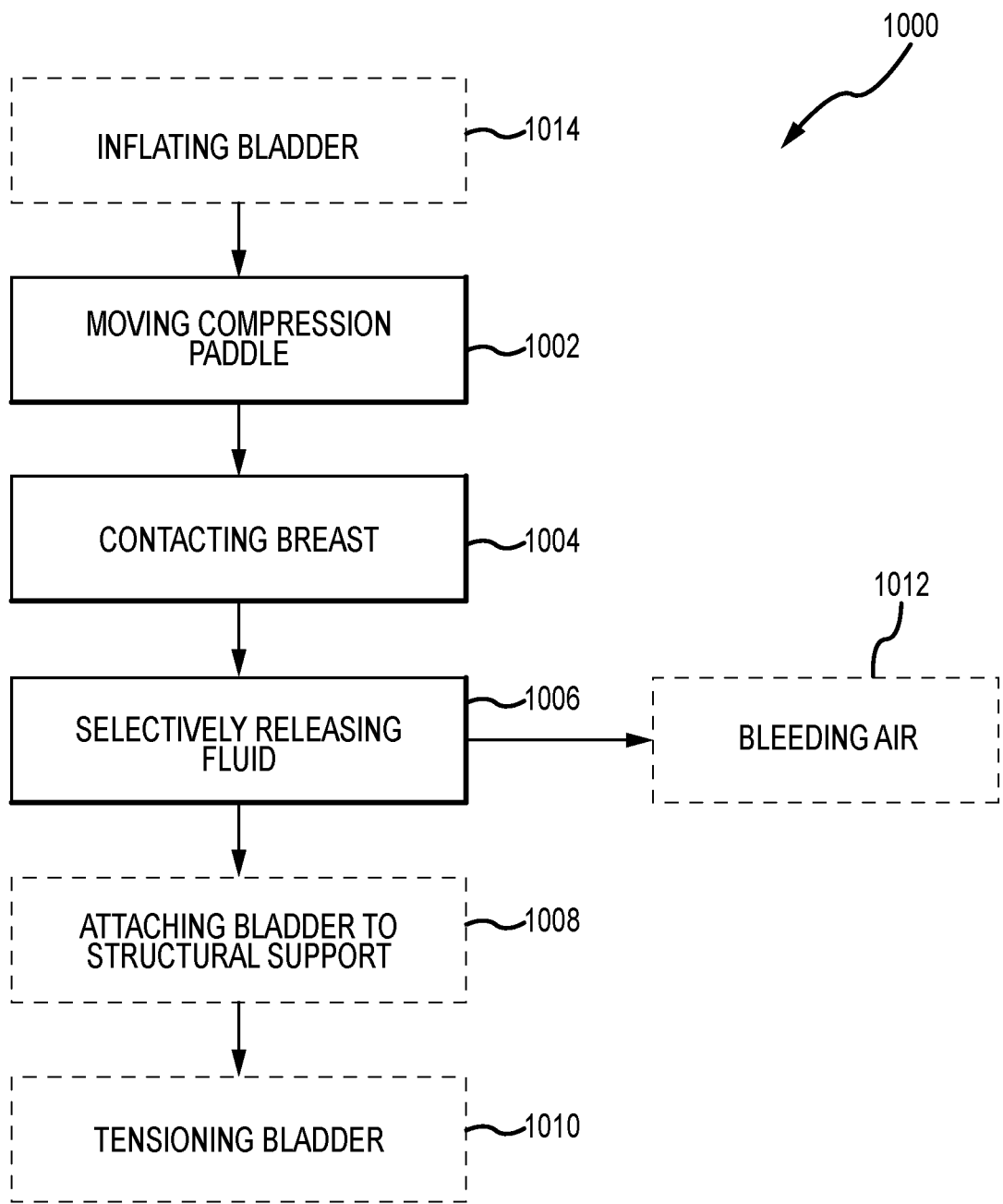
FIG. 11 is a flowchart of a method for compressing a breast for an imaging procedure.

FIG. 11 is a flowchart of a method 1000 for compressing a breast for an imaging procedure on an x-ray imaging system. The method 1000 begins with moving a compression element towards a support platform (operation 1002). The compression element may include a structural support and an inflatable bladder that is filled with a fluid. The breast is then contacted with the compression element such that an initial compressive load is applied to the breast, and the breast is at least partially compressed between the compression element and the support platform (operation 1004). Upon reaching a predetermined compressive force on the breast, at least a portion of the fluid is selectively released from the inflatable bladder such that any further applied compressive load does not increase the compressive force on the breast (operation 1006). In some examples, the method 1000 may further include attaching the inflatable bladder to the structural support (operation 1008) and then tensioning the inflatable bladder between a pair of arms (operation 1010). In other examples, selectively releasing fluid (operation 1006) may include bleeding air to the atmosphere (operation 1012). In still other examples, before moving the compression element (operation 1002), the inflatable bladder can be inflated with the fluid (operation 1014).

The breast compression elements 800, 900 described herein enables the breast compression force of the x-ray imaging system to be controllable such that over-compression of the patient's breast is reduced or prevented. Therefore, patient comfort is increased, while maintaining sufficient breast compression for immobilization and imaging. The inflatable bladder can be inflated and configured to selectively release fluid, for example, through the bleed valve, to reduce over-compression forces on the patient's breast. In other examples, the inflatable bladder can be configured to selectively receive fluid during the breast compression procedures to reduce over-compression forces on the patient's breast. The structural support that the inflatable bladder is coupled to, provides sufficient rigid structure to facilitate breast compression and immobilization with the inflatable bladder.

This disclosure describes some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

The invention claimed is:

1. A breast compression paddle for use in an imaging system, the breast compression paddle comprising:
   a compression surface; and
   a jacket comprising at least one inflatable chamber disposed adjacent to the compression surface and a sheet covering at least a portion of the compression surface, wherein the at least one inflatable chamber is configured to selectively inflate and induce the sheet to slide along the compression surface.

2. The breast compression paddle of claim 1, wherein the sheet comprises at least one cushioning chamber covering at least a portion of the compression surface.

3. The breast compression paddle of claim 2, wherein the at least one cushioning chamber is configured to selectively inflate.

4. The breast compression paddle of claim 2, wherein the at least one cushioning chamber is configured to inflate to a pressure that is lower than a pressure of the at least one inflatable chamber.

5. The breast compression paddle of claim 2, wherein the inflation pressure of the at least one inflatable chamber and the inflation pressure of the at least one cushioning chamber are independently controlled.

6. The breast compression paddle of claim 2, wherein the at least one cushioning chamber comprises a plurality of chambers.

7. The breast compression paddle of claim 2, wherein the breast compression paddle further comprises a bracket or integral feature having a recess defined adjacent to the compression surface, wherein the at least one inflatable chamber is disposed proximate the bracket or integral feature and is configured to selectively inflate at least partially into the recess.

8. The breast compression paddle of claim 1, wherein the sheet is configured to slide along the compression surface substantially simultaneously with the at least one inflatable chamber selectively inflating.

9. The breast compression paddle of claim 1, further comprising a top surface opposite the compression surface, wherein the jacket substantially surrounds the top surface and the compression surface.

10. The breast compression paddle of claim 9, further comprising a bracket or integral feature, and wherein the jacket further comprises a first edge coupled to the bracket or integral feature adjacent the top surface.

11. An imaging system comprising:
an imaging source;
an imaging receptor defining an imaging area; and
a breast compression unit comprising:
  a breast compression paddle comprising a first compression surface;
  a platform comprising a second compression surface, wherein the breast compression paddle is configured to move in relation to the platform to compress a patient's breast between the first compression surface and the second compression surface; and
  a paddle jacket disposed on the breast compression paddle such that the first compression surface is at least partially covered, the paddle jacket comprising at least one inflatable chamber and a sheet, wherein the at least one inflatable chamber is configured to selectively inflate and induce the sheet to slide along the first compression surface.

12. The imaging system of claim 11, further comprising a platform jacket disposed on the platform such that the second compression surface is at least partially covered, the platform jacket comprising at least one inflatable chamber and a sheet, wherein the at least one inflatable chamber is configured to selectively inflate and induce the sheet to slide along the second compression surface.

13. The imaging system of claim 12, wherein the paddle jacket is independently inflatable from the platform jacket.

14. The imaging system of claim 11, further comprising a fluid source configured to deliver a flow of fluid to the paddle jacket for the selective inflation of the at least one inflatable chamber.

15. The imaging system of claim 11, wherein the paddle jacket is removably disposed on the breast compression paddle.

16. The imaging system of claim 11, wherein the breast compression paddle is removable from the breast compression unit.

17. A method of compressing a breast in an imaging system including a jacket having at least one inflatable chamber and a sheet, the method comprising:
compressing a breast between a compression paddle and a platform; and
selectively inflating the at least one inflatable chamber of the jacket disposed on the breast compression paddle such that the sheet slides along a compression surface and pulls at least some breast tissue away from a patient's chest wall and into an imaging area.

18. The method of claim 17, wherein the sheet includes at least one cushioning chamber disposed below the compression surface, the method further comprising after the breast is compressed between the compression paddle and the platform selectively inflating the at least one cushioning chamber.

19. The method of claim 18, wherein the at least one inflatable chamber is selectively inflated to a different pressure than a pressure of the at least one cushioning chamber.

20. The method of claim 17 further comprising:
removably attaching the jacket on the breast compression paddle; and
coupling in fluid communication the jacket to a fluid source.

* * * * *